(12) United States Patent
Schilling et al.

(10) Patent No.: US 12,227,654 B2
(45) Date of Patent: Feb. 18, 2025

(54) PVD-ALUMINUM PIGMENT DISPERSION AND COSMETIC FORMULATIONS

(71) Applicant: ECKART GmbH, Hartenstein (DE)

(72) Inventors: Christine Schilling, Hartenstein (DE); Andrea Wolfring, Hartenstein (DE); Michaela Gerstacker, Hartenstein (DE)

(73) Assignee: ECKART GmbH, Hartenstein (DE)

( * ) Notice: Subject to any disclaimer, the term of this patent is extended or adjusted under 35 U.S.C. 154(b) by 1127 days.

(21) Appl. No.: 17/056,974

(22) PCT Filed: Jul. 15, 2019

(86) PCT No.: PCT/EP2019/068987
§ 371 (c)(1),
(2) Date: Nov. 19, 2020

(87) PCT Pub. No.: WO2020/016171
PCT Pub. Date: Jan. 23, 2020

(65) Prior Publication Data
US 2021/0244634 A1    Aug. 12, 2021

(30) Foreign Application Priority Data
Jul. 16, 2018    (EP) .................................. 18183656

(51) Int. Cl.
| | | |
|---|---|---|
| C09C 1/64 | (2006.01) | |
| A61K 8/02 | (2006.01) | |
| A61K 8/04 | (2006.01) | |
| A61K 8/25 | (2006.01) | |
| A61K 8/26 | (2006.01) | |
| A61K 8/37 | (2006.01) | |
| A61K 8/55 | (2006.01) | |
| A61K 8/92 | (2006.01) | |
| A61Q 1/02 | (2006.01) | |
| A61Q 1/04 | (2006.01) | |
| A61Q 1/10 | (2006.01) | |

(52) U.S. Cl.
CPC .................. *C09C 1/64* (2013.01); *A61K 8/04* (2013.01); *A61K 8/26* (2013.01); *A61K 8/375* (2013.01); *A61K 8/55* (2013.01); *A61K 8/92* (2013.01); *A61Q 1/02* (2013.01); *C09C 1/644* (2013.01); *A61K 8/025* (2013.01); *A61K 8/0254* (2013.01); *A61K 8/25* (2013.01); *A61K 2800/437* (2013.01); *A61K 2800/438* (2013.01); *A61K 2800/612* (2013.01); *A61K 2800/651* (2013.01); *A61Q 1/04* (2013.01); *A61Q 1/10* (2013.01); *C09C 2220/20* (2013.01)

(58) Field of Classification Search
CPC ....... C09C 1/64; C09C 1/644; C09C 2220/20; A61K 8/04; A61K 8/025; A61K 8/0254; A61K 8/25; A61K 8/26; A61K 8/375; A61K 8/55; A61K 8/92; A61K 2800/437; A61K 2800/438; A61K 2800/612; A61K 2800/651; A61Q 1/02; A61Q 1/04; A61Q 1/10
See application file for complete search history.

(56) References Cited

U.S. PATENT DOCUMENTS

| | | |
|---|---|---|
| 3,949,139 A | 4/1976 | Dunning et al. |
| 4,168,986 A | 9/1979 | Venis, Jr. |
| 4,321,087 A | 3/1982 | Levine et al. |
| 5,624,076 A | 4/1997 | Miekka et al. |
| 5,672,410 A | 9/1997 | Miekka et al. |
| 6,317,947 B1 | 11/2001 | Ruschmann et al. |
| 6,692,830 B2 | 2/2004 | Argoitia et al. |
| 8,911,546 B2 | 12/2014 | Henglein et al. |
| 8,979,972 B2 | 3/2015 | Chung et al. |
| 10,745,575 B2 | 8/2020 | Becker et al. |
| 2003/0008068 A1 | 1/2003 | Josephy et al. |
| 2003/0031870 A1 | 2/2003 | Argoitia et al. |
| 2007/0199478 A1 | 8/2007 | Schlegl et al. |
| 2008/0131383 A1* | 6/2008 | Kruger ..................... A61K 8/55 514/769 |
| 2008/0274354 A1 | 11/2008 | Rettker |
| 2019/0077963 A1 | 3/2019 | Schilling et al. |

FOREIGN PATENT DOCUMENTS

| | | | |
|---|---|---|---|
| EP | 1613702 A2 | 1/2006 | |
| EP | 1694288 A1 | 8/2006 | |
| EP | 1796794 A1 | 6/2007 | |
| EP | 2083052 A1 * | 7/2009 | ................ B41J 2/01 |
| EP | 2143769 A1 | 1/2010 | |
| JP | 2016044206 A | 4/2016 | |

(Continued)

OTHER PUBLICATIONS

H. Noureddini, et al. "Viscosities of Vegetable Oils and Fatty Acids" JAOCS, vol. 69, No. 12 (Dec. 1992), pp. 1189-1191 (Year: 1992).*
Noureddini, H. "Viscosities of Vegetable Oils and Fatty Acids" JAOCS, vol. 69, No. 12 (Dec. 1992) pp. 1189-1191 (Year: 1992).*
International Search Report and Written Opinion for International Patent Application No. PCT/EP2019/068987 dated Sep. 11, 2019 (11 pages).

*Primary Examiner* — Pegah Parvini
(74) *Attorney, Agent, or Firm* — Fitch, Even, Tabin & Flannery LLP

(57) ABSTRACT

This invention is directed to an effect pigment dispersion comprising a PVD-aluminum pigment, a leafing additive and an oil suitable for cosmetic skin care or color cosmetic applications, wherein a) the amount of the PVD-aluminum pigment is in a range of 8 to 30 wt.-%, b) the amount of the oil is in a range of 70 to 90 wt.-%, each based on the total weight of the effect pigment dispersion and c) the leafing additive is partly adsorbed on the surface of the PVD-aluminum pigment and partly an excess additive dissolved in the oil, wherein the amount of excess leafing additive is in a range of 0 to 25 wt.-%, based on the weight of PVD aluminum pigment. Further cosmetic skin care of color cosmetic formulations containing this effect pigment dispersion are described.

26 Claims, No Drawings

(56) References Cited

FOREIGN PATENT DOCUMENTS

| | | | |
|---|---|---|---|
| WO | 2007014680 A1 | 2/2007 | |
| WO | WO-2008007334 A2 * | 1/2008 | ............... A61K 8/02 |
| WO | 2009074963 A2 | 6/2009 | |
| WO | 2011018369 A2 | 2/2011 | |
| WO | 2011148328 A2 | 12/2011 | |
| WO | 2011161020 A2 | 12/2011 | |
| WO | 2013010776 A1 | 1/2013 | |
| WO | 2016189519 A1 | 12/2016 | |
| WO | 2017019480 A1 | 2/2017 | |
| WO | 2017036542 A1 | 3/2017 | |
| WO | 2017037716 A2 | 3/2017 | |
| WO | 2017080988 A1 | 5/2017 | |
| WO | 2017178610 A1 | 10/2017 | |

* cited by examiner

PVD-ALUMINUM PIGMENT DISPERSION AND COSMETIC FORMULATIONS

The present invention relates to dispersions of PVD-aluminum pigments suitable for cosmetic skin care and color cosmetic applications, to their production method and to cosmetic skin care and color cosmetic applications containing the dispersion and to the production method of this cosmetic formulations.

Effect pigments such as pearlescent pigments or conventional metal platelet pigments obtained by grinding are available in powder form and are therefore easily processable in cosmetic skin formulations. However, conventional metal platelet pigments do not exhibit the very high gloss and brilliance of PVD metal pigments. Such PVD pigments can have a so-called "mirror" effect and they represent the high-class metallic effect pigments with respect to their optical appearance.

EP 1694288 A1 discloses cosmetic formulations such as nail polishes or lip gloss containing diffractive PVD-pigments. The PVD-pigments are used here throughout as dispersions in organic solvents.

Leafing PVD pigments were described in EP 1796794 A1. In WO 2017/178610 A1 a nail polish was disclosed offering improvements for the leafing PVD-pigments. Again the PVD-pigments are used throughout as dispersions in organic solvents. Leafing PVD pigments have unpolar additives adsorbed on their surface. Due to an intended incompatibility of these pigments to the other components of the formulation they are located after application on the top of the applied nail polish. This leads to an extremely brilliant metallic effect.

Such leafing metallic pigments are also well known from the lacquer or printing industry.

PVD aluminum effect pigments are used in many fields such as coatings, printing inks or cosmetics. Due to the high agglomeration tendency of the PVD aluminum pigments, they virtually cannot be dried to obtain a pigment powder. Commercially they are sold as dispersions in organic solvents in concentrations of typically 10 to 20 wt.-%. Typical solvents used are, for example, methoxy propanol acetate, n-propyl acetate, isopropyl acetate, ethyl acetate, methoxy propanol or ethanol butyl glycol. The high amount of solvent enables easy use in some cosmetic formulations, such as nail polish, especially if compatible solvents like e.g. ethyl acetate are chosen. Many of the solvents used do not comply with cosmetic regulations for skin care and color cosmetic applications. Even if they do comply, the high amount of solvent typically used makes a formulation, for example in a lipstick, impossible. In other cases, such as lip-gloss or eye shadow, a formulation may be possible, but only with very restricted parameters in respect to the achievable concentration of the PVD-pigment. The cosmetic formulations obtained are generally too liquid because of the high amount of organic solvents. The organic solvents can furthermore lead to skin irritations and particularly to unfavorable drying of the skin. Cosmetic formulations with high amounts of organic solvents do not comply with the general trend in cosmetic towards natural ingredients. Additionally, manufacturers of cosmetic formulations are usually not equipped for dealing with excess of organic solvents.

Thus, there is a need to provide a PVD aluminum effect pigment in a form acceptable for cosmetic skin applications and color cosmetic applications, other than nail polish, exhibiting a high gloss. The PVD aluminum pigments should be essentially free of agglomerates. This form should allow the formulation of such applications in a versatile manner with respect to the kind of the pigment used and to the concentrations of all components. The formulations should provide a high metallic gloss and a pleasant skin feeling.

These problems are solved by providing an effect pigment dispersion comprising a PVD-aluminum pigment, a leafing additive and an oil suitable for cosmetic skin care or color cosmetic applications, wherein
 a) the amount of the PVD-aluminum pigment is in a range of 8 to 30 wt.-%,
 b) the amount of the oil is in a range of 70 to 90 wt.-%, each based on the total weight of the effect pigment dispersion and
 c) the leafing additive is partly adsorbed on the surface of the PVD-aluminum pigment and partly present as an excess additive dissolved in the oil, wherein the amount of excess leafing additive is in a range of 0 to 25 wt.-%, based on the weight of PVD aluminum pigment.

Additionally, there is further a need to provide cosmetic skin applications and color cosmetic applications without organic solvent.

There is further a need to provide a method of producing the effect pigment dispersion and a method of producing the cosmetic skin applications and cosmetic color application without organic solvent.

These needs are solved by the following aspects and their respective claims.

The invention has been made in order to solve the above described problems and needs and can be realized by the following aspects:

A first aspect is directed to an effect pigment dispersion comprising a PVD-aluminum pigment, a leafing additive and an oil suitable for cosmetic skin care or color cosmetic applications, wherein
 a) the amount of the PVD-aluminum pigment is in a range of 8 to 30 wt.-%,
 b) the amount of the oil is in a range of 70 to 90 wt.-%, each based on the total weight of the effect pigment dispersion and
 c) the leafing additive is partly adsorbed on the surface of the PVD-aluminum pigment and partly an excess additive dissolved in the oil, wherein the amount of excess leafing additive is in a range of 0 to 25 wt.-%, based on the weight of PVD aluminum pigment.

According to a preferred aspect 2 of the invention, the effect pigment dispersion according to aspect 1, is characterized in that residual organic solvent is present in an amount of less than 5 wt.-% of the whole dispersion.

According to a preferred aspect 3 of the invention, the effect pigment dispersion according to any of the preceding aspects, is characterized in that a binder is additionally present in an amount of less than 1 wt.-%, based on the total weight of the effect pigment dispersion.

According to a preferred aspect 4 of the invention, the effect pigment dispersion according to any of the preceding aspects, is characterized in that the amount of additional dispersing additives in the dispersion is in a range of 0 to less than 0.2 wt.-% and preferably 0 wt.-%, based on the weight of the PVD-aluminum pigment.

According to a preferred aspect 5 of the invention, the effect pigment dispersion according to any of the preceding aspects, is characterized in that additionally fillers from the group natural or synthetic mica, glass flakes, glass spheres, silica spheres, silica flakes, alumina spheres, alumina flakes or talc are contained in the dispersion.

According to a preferred aspect 6 of the invention, the effect pigment dispersion according to any of the preceding aspects, is characterized in that the weight of the PVD-aluminum pigment, the leafing additive, the oil suitable for cosmetic skin care or color cosmetic applications and optionally the filler all together is at least 90 wt.-%, based on the total weight of the effect pigment dispersion.

According to a preferred aspect 7 of the invention, the effect pigment dispersion according to any of the preceding aspects, is characterized in that the amount of PVD aluminum pigment is in a range of 12.5 to 25 wt-% and the amount of the oil in a range of 75 to 87.5 wt.-%, each based on the total weight of the effect pigment dispersion.

According to a preferred aspect 8 of the invention, in the effect pigment dispersion according to any of the preceding aspects, the leafing PVD-aluminum effect pigment has a leafing agent adsorbed on its surface selected from the group consisting of a) phosphoric esters of the formula (I):

b) phosphonic acid ester of the general formula (II):

wherein m=1 to 3 and any mixture thereof and R, $R^1$, $R^2$ and $R^3$ have the meaning:

R=linear and/or branched alkyl with a carbon chain in a range of $C_8$ to $C_{20}$, $R^1$=H, linear and/or branched alkyl with a carbon chain in a range of $C_1$ to $C_6$, preferably $C_1$ to $C_3$, wherein $R^1$ can in case of m=1 be identical of different, and $R^2$=$R^3$=H, linear and/or branched alkyl with a carbon chain in a range of $C_1$ to $C_6$, preferably $C_1$ to $C_3$, wherein $R^2$ and $R^3$ can be identical or different, or c) a fatty acid with the general formula (III)

wherein $R^7$ is a linear and/or branched alkyl with a carbon chain in a range of $C_{12}$ to $C_{26}$, preferably in a range of $C_{14}$ to $C_{24}$, or mixtures thereof, or d) an organofunctional silane according to formula (IV):

wherein $R^7$ is a linear of branched alkyl moiety with a carbon chain in a range of $C_1$ to $C_4$, preferably $C_1$ to $C_3$ and most preferably $C_1$ to $C_2$ and R" is a linear or branched alkyl or aryl moiety with a carbon chain in a range of $C_8$ to $C_{24}$, preferably in a range of $C_{12}$ to $C_{18}$.

According to a preferred aspect 9 of the invention, the effect pigment dispersion according to aspect 8, is characterized in that the leafing agent is selected from the group consisting of a) phosphoric esters of the formula (I), wherein m=1 or 2 or a mixture thereof, $R^1$=H and R is a linear and/or branched alkyl with a carbon chain in a range of $C_{12}$ to $C_{18}$ or b) phosphonic acids of the formula (II), wherein $R^2$=$R^3$=H and R is a linear or branched alkyl with a carbon chain in a range of $C_{10}$ to $C_{13}$ and more preferably in a range of $C_{12}$ to $C_{16}$.

According to a preferred aspect 10 of the invention, the effect pigment dispersion according to any of the preceding aspects, is characterized in that the amount of aromatic compounds in the oil is less than 0.5 wt.-%, based on the total weight of oil.

According to a preferred aspect 11 of the invention, the effect pigment dispersion according to any of the preceding aspects, is characterized in that the oil suitable for cosmetic skin applications has a boiling point of at least 75° C. at normal conditions.

According to a preferred aspect 12 of the invention, the effect pigment dispersion according to any of the preceding aspects, is characterized in that the oil suitable for cosmetic skin care or color cosmetic applications is selected from the following types:

a) triglycerides consisting of fatty acid esters of glycerol which have an average chain length ranging from $C_8$ to $C_{36}$, these chains being linear or branched and saturated or unsaturated and mixtures thereof;

b) mineral oils with very high purity, wherein the hydrocarbon chains have an average length of at least 14 C-atoms;

c) alcohols based on alcohols other than glycerine or hydrocarbon-based (fatty) esters originating from carboxylic and alcoholic components other than glycerol according to formula (V):

wherein:

x is an integer and x=1 to 6, representing the number of acidic groups for alcoholic components with more than one OH-group, $R^4(COO)_y$ represents a carboxylic acid residue comprising from 2 to 40 carbon atoms, wherein $R^4$ can be a linear or branched, saturated or unsaturated hydrocarbon chain or phenyl, the integer y can be 1 to 3, and represents the number of COOH groups of the original acidic component;

$R^5$ represents a hydrocarbon-based chain originating from the alcoholic component or components containing from 1 to 40 carbon atoms, which can comprise a —$CH_2$—O—$CH_2$—ether unit or which can be or comprise a PPG or PEG element represented by the formula (VI):

wherein $R^6$ is H or $CH_3$ and n=1 to 10;

d) fatty alcohols containing from 12 to 26 carbon atoms;

e) synthetic ethers containing from 10 to 40 carbon atoms or f) dialkyl carbonates, wherein the two alkyl chains can be identical or different.

According to a preferred aspect 13 of the invention, the effect pigment dispersion according to any of the preceding aspects, is characterized in that the oil suitable for cosmetic skin care or color cosmetic applications is selected from the group consisting of Caprylic/Capric Triglyceride, Ricinus Communis Seed Oil, Prunus Amygdalus Dulcis Oil, Coriandrum Sativum (Coriander) Seed Oil, Zea Mays (Corn) Oil, Triticum Vulgare (Wheat) Germ Oil, Simmondsia Chinensis (Jojoba) Seed Oil, Vitis Vinifera (Grapd) Seed Oil, Oenothera Biennis (Evening Primrose) Oil, Prunus Armeniaca (Apricot) Kernel Oil, Persea Gratissima (Avocado) Oil, (Hydrogenatec) Palm Kernel Oil, Orbignya Oleifera (Babassu) Seed Oil, Ocimum Basillicum (Basil) Oil, Corylus Americana (Hazel) Seed Oil, Cannabis Sativa Seed Oil, Juglans Regia (Walnut) Seed Oil, Arachis Hypogaea (Peanut) Oil, Oryza Sativa (Ricd) Bran Oil, Rosa Canina Fruit Oil, Carthamus Tinctorius (Safflower) Seed Oil, Sesamum Indicum (Sesame) Seed Oil, Aloe Barbadensis Leaf Extract, Camelina Sativa Seed Oil, Olea Europaea (Olivd) Fruit Oil, Helianthus Annuus (Sunflower) Seed Oil, Argania Spinosa Kernel Oil, Cucurbita Pepo Seed Oil, Glycine Soja (Soybean) Oil, Hydrogenated Rapeseed Oil, Hydrogenated Soybean Oil, Hydrogenated Cottonseed Oil, Hydrogenated Vegetable Oil, Paraffinum Liquidium, Isohexadecane, Hydrogenated Polyisobutene, Glyceryl Undecylenate, Propanediol Dicaprylate,Propylene Glycol Dibenzoate, Neopentyl Glycol Diheptanoate, Isononyl Nonanoate, Isononyl Isononanoate, 2-Ethylhexyl 4-diheptanoate, C12-15 Alkyl Benzoate, Isostearyl Isostearate, Hexyl laurate, Octyldodecanol, Isopropyl Myristate, Myristyl myristate, Diisopropyl adipate, Decyl Isostearate (and) Isostearyl Isostearate, Oleyl Oleate, Ethylhexyl Palmitate, Tridecyl octanoate Cetyl octanoate, Propylene glycol dioctanoate, Isotridecyl Isononanoate, Octyl isononanoate, Isodecyl neopentanoate, Isostearyl Neopentanoate, 2-Octyldodecyl neopentanoate, Isopropyl stearate, Isopropyl isostearate, Octyl stearate, Isooctyl stearate, 2-Ethylhexyl hydroxystearate, Isocetyl stearate, 2-Octyldodecyl stearate, Octyldodecyl Stearoyl Stearate, Isopropyl Palmitate, 2-Ethylhexyl palmitate, Heptyl Undecylenate, Isostearyl heptanoate, Pentaerythrityl Tetrabehenate, Isostearyl behenate, Pentaerythritol Tetraisostearate, Neopentyl Glycol Diheptanoate (and) Isododecane, Pentaerythrityl Tetraethylhexanoate, Dipentaerythrityl Pentaisononanoate, Tetraethylene glycol diheptanoate, Neopentyl Glycol Diheptanoate, Propylene glycol 2-ethyl hexanoate, Dicapryl Succinate, Isopropyl lauroyl sarcosinate, Triisostearyl Citrate, Diisostearyl Malate, Bis-Diglyceryl Polyacyladipate-1, Diisopropyl Dimer Dilinoleate, Diisopropyl Sebacate, Trimethylolpropane Tricaprylate/Tricaprate, Diheptyl Succinate (and) Capryloyl Glycerin/Sebacic Acid Copolymer, Polyester 4, cocyl adipidic acid/trimethylolpropane copolymer, Octyldodecanol, 2-butyloctanol, 2-hexyldecanol, 2-undecylpentadecanol, isohexacosanol, oleyl alcohol, Dicaprylyl Ether, Dicaprylyl Carbonate, Oleyl erucate, PPG-3 Benzyl Ether Ethylhexanoate, PPG-3 Benzyl Ether Myristate and mixtures thereof.

According to a preferred aspect 14 of the invention, the effect pigment dispersion according to any of the preceding aspects, is characterized in that the dispersion does not contain additional delaminated silicate-based platelets.

According to a preferred aspect 15 of the invention, the effect pigment dispersion according to any of the preceding aspects, is characterized in that the dispersion is not encapsulated by microcapsules made from polymers.

According to a preferred aspect 16 of the invention, the effect pigment dispersion according to any of the preceding aspects, is characterized in that the PVD-aluminum effect pigment is a leafing pigment with planar surfaces. According to a preferred aspect 17 of the invention, the effect pigment dispersion according to any of the preceding aspects 1 to 15, is characterized in that the leafing PVD-aluminum effect pigment comprises an embossed structure with a period in a range from 5,000 to 20,000 lines per cm.

According to a preferred aspect 18 of the invention, the effect pigment dispersion according to any of the preceding aspects, is characterized in that the PVD-aluminum pigment is coated with a metal oxide in an amount of 0 to less than 5 wt.-%, based on the total weight of the PVD-pigment.

According to an aspect 19, the invention is directed to an effect pigment dispersion according to any of the preceding aspects for use as an effect pigment semi-finished product in a cosmetic skin care or a color cosmetic formulation.

According to an aspect 20, the invention is directed to the use of the effect pigment dispersion of aspects 1 to 18 as a semi-finished product in cosmetic skin or color cosmetic formulations.

According to an aspect 21, the invention is directed to a method of producing the effect pigment dispersion of aspects 1 to 19 comprising the following subsequent steps:

a) providing a leafing PVD-aluminum dispersion in an organic solvent,
b) adding the oil suitable for cosmetic skin care or color cosmetic applications to the dispersion a) and
c) removing the organic solvent, optionally under vacuum.

According to a preferred aspect 22, the invention is directed to a cosmetic skin care or color cosmetic formulation comprising the effect pigment dispersion of aspects 1 to 18, wherein the color cosmetic formulations preferably consist in lip color formulations or in eye color formulations.

According to a preferred aspect 23 of the invention, the cosmetic skin care or color cosmetic formulation according to aspect 22 is characterized in that this formulation is selected from the following groups:

a) skin care selected from the group consisting of lotions, moisturizers, primers, self-tanners, face masks and face treatments, body paints, men's skin care, anti-age creams, treatment creams, balm and blemish creams (BB creams), color or complexion correction creams (CC creams) and diminish and disguise creams (DD creams);
b) lip color formulations selected from the group consisting of lip gloss, lip stick, liquid lip stick, clear lip stick, lip cream, lip tint, lip lacquer, lip color, lip balm, lip glaze, lip paint, lip oil, lip stain, lip liner, lip polish and lip plumper.
c) eye color formulations selected from the group consisting of pressed eye shadow, cream eye shadow, mousse eye shadow, eye shadow gel, cream-to-powder eye shadow, eye shadow pencil, liquid eye shadow, loose eye shadow, eye shadow powder, liquid eyeliner, eyeliner stick, eyeliner cream, eyeliner gel, mascara, brow gel, brow pencil, brow definer, tattoo Liner or lash primer.

According to a preferred aspect 24 of the invention, the cosmetic skin care or color cosmetic formulation according to aspects 22 or 23 is characterized in that the dispersion does not contain additional delaminated silicate-based platelets.

According to an aspect 25, the invention is directed to a method of producing a cosmetic skin or color cosmetic formulation according to aspects 22 to 24 comprising the steps:

a) preparing a phase A by mixing typical ingredients characteristic for the formulation,
b) providing a phase B comprising the effect pigment dispersion of claims 1 to 18,
c) mixing and homogenizing phase A and phase B, optionally at temperatures above 20° C. under low mechanical stress conditions and finally
d) pouring or filling the formulation into an appropriate container or packaging.

Leafing-PVD Aluminum Pigment:

Commercially available PVD-aluminum pigments as usually produced are typically non-leafing pigments. To achieve the desired optical properties, such as the mirror effect, they need to be turned into leafing effect pigments by using appropriate leafing additives, which adsorb on the pigments surface.

The term "adsorbed" in this invention is meant to comprise any kind of bonding of the leafing additive to the PVD-aluminum pigment surface such as chemisorption, physisorption or the like.

Preferably the leafing PVD-aluminum effect pigment has a leafing agent adsorbed on its surface selected from the group consisting of a) phosphoric acid esters of the formula (I):

$$(R-O)_m-P(O)(OR^1)_{(3-m)} \quad (I)$$ or b) phosphonic acids of the general formula (II):

$$R-P(O)(OR^2)(OR^3) \quad (II)$$

Herein m=1 to 3 and any mixture thereof and R, $R^1$, $R^2$ and $R^3$ have the meaning:

R=linear and/or branched alkyl with a carbon chain in a range of $C_8$ to $C_{20}$, $R^1$=H, linear and/or branched alkyl with a carbon chain in a range of $C_1$ to $C_6$, preferably $C_1$ to $C_3$, wherein $R^1$ can in case of m=1 be identical of different, and $R^2$=$R^3$=H, linear and/or branched alkyl with a carbon chain in a range of $C_1$ to $C_6$, preferably $C_1$ to $C_3$, wherein $R^2$ and $R^3$ can be identical or different.

In a further embodiment c) the leafing additive can be a fatty acid with the general formula (III)

$$R'-COOH \quad (III)$$

Herein R' is a linear and/or branched alkyl with a carbon chain in a range of $C_{12}$ to $C_{26}$, preferably in a range of $C_{14}$ to $C_{24}$, more preferably in a range of $C_1$ to $C_{22}$ and most preferably in a range of $C_{13}$ to $C_{20}$, or mixtures thereof.

Preferably the leafing agent is selected from the group consisting of phosphoric esters of the formula (1), wherein m=1 or 2 or a mixture thereof, $R^1$=H and R is a linear or branched alkyl with a carbon chain in a range of $C_{12}$ to $C_{13}$ more preferably $C_{14}$ to $C_{16}$ and particularly $C_{16}$.

In another preferred embodiment the leafing agent is selected from the group consisting of phosphonic acids of the formula (II), wherein $R^2$=$R^3$=H and R is a linear or branched alkyl with a carbon chain in a range of $C_{10}$ to $C_{13}$ and more preferably in a range of $C_{14}$ to $C_{13}$.

Preferred examples are stearic acid or palmitic acid.

In preferred embodiments the leafing-additives of the kind of formula (1) or (II) are dilaurylphosphonic acid, monolaurylphosphonic acid (R=$C_{12}$)) or monocetylphosphoric acid ester or dicetylphosphoric acidester (R=$C_{16}$)) or mixtures thereof.

In a further embodiment the leafing additive can be an organofunctional silane according to formula (IV):

$$R''-Si(OR^7)_3 \quad (IV)$$

Herein $R^7$ is a linear of branched alkyl moiety with a carbon chain in a range of $C_1$ to $C_4$, preferably $C_1$ to $C_3$ and most preferably $C_1$ to $C_2$. R'' is a linear or branched alkyl or aryl moiety with a carbon chain in a range of $C_8$ to $C_{24}$, preferably in a range of $C_{12}$ to $C_{13}$.

The PVD-aluminum pigment used before the addition of a leafing-additive is preferably an uncoated effect pigment. In other embodiments the PVD-aluminum pigment is coated with a metal oxide in an amount of less than 5 wt.-%, based on the total weight of the PVD-pigment. A preferred metal oxide is silica. Such metal oxide coated PVD aluminum pigments may be advantageous especially if an organofunctional silane is used as leafing additive, as these silanes can be well bonded to a metal oxide surface. The amount of metal oxide should be as low as possible in order not to reduce the hiding power of the effect pigment and not to alter the brilliant optical properties of the PVD pigment. Therefore, the amount of metal oxide is preferably lower than 4 wt.-%, more preferably lower than 3 wt.-% and most preferably lower than 2 wt.-%. It can be in a range of 0 to 4 wt.-% or 1 to 4 wt.-% or 1.5 to 3 wt.-%.

The PVD-aluminum effect pigment can be a leafing effect pigment with planar (flat) surfaces. Such pigments are well known for their high reflection and thus high brilliance, as the pigment surfaces are almost perfectly flat and have a minimum of diffuse reflection due to edge effects. In the case of a leafing effect pigment, the strong gloss, brilliance and "mirror" effect in the cosmetic applications will be even enhanced. Furthermore, a leafing effect can be observed if the PVD aluminum pigment dispersion is packed in a transparent packaging like e.g. glass container.

The flat PVD-aluminum effect pigments preferably have a median size $d_{50}$ in a range of 5 to 50 μm. More preferably, the $d_{50}$ is in a range of 7.5 to 30 μm and most preferably is in a range of 8 to 20 μm.

Below a $d_{50}$ of 5 μm the optical properties get less favorable. Above a $d_{50}$ of 50 μm the pigments are in some cases not conform with cosmetic regulations and they may worsen the skin feeling in the cosmetic application.

The $d_{50}$-value is determined using laser granulometry, preferably by using a Horiba LA-930 (Retsch Technology, Germany) instrument. Here a volume averaged particle size distribution based on equivalent spheres is determined using the Fraunhofer diffraction approximation.

The average thickness of the flat PVD-aluminum pigments is expressed by the median thickness $h_{50}$ and is preferably in a range of 15 nm to 80 nm. More preferably, $h_{50}$ is in a range of 20 to 60 nm and most preferably is in a range of 20 to 40 nm. Below a $h_{50}$ of 15 nm the pigments become more and more transparent and dark which decreases the desired silvery brilliance and mirror effect. Above $h_{50}$=80 nm the orientation of the PVD-pigments can be less optimal, which lowers the gloss and brilliance. Furthermore the hiding power is reduced significantly.

The median thickness $h_{50}$ is determined by counting of pigment thicknesses in a SEM. Details of the method can be found in EP 1613702 B1 (paragraphs [0125] and [0126]). The $h_{50}$-value is the thickness where 50% of all particles counted are below this value. At least 100 particles are counted.

In other embodiments the leafing PVD-aluminum effect pigments are diffractive pigments, which comprise an embossed structure with a period in a range from 5,000 to 20,000 lines per cm. Such pigments exhibit a so-called "rainbow" effect, as these pigments deconstruct incoming white light into different optical wavelengths by diffraction phenomena. Additionally, wavelengths in the UV- or IR-range can be diffracted as well. Such pigments are known from U.S. Pat. Nos. 5,624,076, 5,672,410 A U.S. Pat. No. 6,692,830 B2 or US 20080274354 A1 wherein these effects are well described. A leafing embossed PVD pigment will exhibit the rainbow effect to a great extent.

The embossed structure exhibits a periodic pattern with diffractive elements. Preferably the periodic structure comprises 5.000 to 20.000 diffractive elements/cm, more preferably 9.000-18.000 diffractive elements/cm and most preferably 12.000-16.000 diffractive elements/cm.

The periodicity determines basically the diffracted wavelengths of incoming light. This can be calculated according to known formulas as described in U.S. Pat. No. 6,692,830 B2, for example.

The diffractive elements can have a geometry of symmetrical triangles, asymmetrical triangles, groove shapes, rectangular structures, spheres, undulated lines, conus, truncated cones, burlings, prism, pyramids, cylinder, halfspheres and combinations of these.

In preferred embodiments the embossed structure, preferably a line structure, comprises preferably a minimum depth, in order to achieve a clearly observable effect. Otherwise the physical effect of diffraction may be inadequately developed. The diffractive structure preferably has a depth (measured as "hill" to "valley") of at least 40 nm, further preferably in a range of 40 to 600 nm, more preferably in a range of 50 to 400 nm and most preferably in a range of 100 to 250 nm. Above 600 nm the stability of the structure may not be given any more.

Additionally to the depth of the embossed structure, the diffractive PVD aluminum pigments have a primary thickness h. The median primary thickness $h_{50}$ is preferably in a range of 20 nm to 80 nm and more preferably in a range of 30 to 60 nm. $h_{50}$ is determined by the same method as for the flat PVD aluminum pigments.

Below a $h_{50}$ of 20 nm the PVD pigment can become too dark and the mechanical stability necessary to maintain the embossed structure may be lost. Above a $h_{50}$ of 80 nm the same drawbacks as for flat PVD aluminum pigments may occur.

The depth of the diffractive structure may therefore exceed the thickness of the diffractive PVD aluminum pigment.

The median size $d_{50}$ of the embossed PVD aluminum pigments is preferably in a range of 5-120 µm, more preferably in a range of 10-75 µm and most preferably in a range of 15-40 µm.

This value is determined in the same manner as for flat PVD pigments.

The sizes may be larger than in case of the flat PVD pigments as the rainbow effect develops better with larger pigment platelets. Larger particles allow more wave trains of reflected light to overlap and therefore enhance the rainbow effect.

The leafing PVD aluminum pigments are produced preferably by first providing a PVD aluminum dispersion in an organic solvent by means known in the state of the art. Briefly, a sheet substrate which has preferably the form of a circular band, is first coated with a peeling layer. This release layer can be made of polymers such as typically a polyvinyl alcohol, polyvinyl butyral, polyethylene glycol, polyacrylic acid, polyacrylamide, cellulose derivative, acrylate polymer, or modified nylon resin. But also peeling layers made by a salt such as NaF are known in the art.

A solution containing a mixture of one or more of the aforementioned release layer substances is applied to the recording medium, and a layer is formed by drying or the like. The thickness of the release layer is preferably in a range of 0.1 to 20 nm.

The release resin layer can be formed using commonly used gravure application, roller application, blade application, extrusion application, dip application, or spin coat method or the like. After applying and drying, the surface can be smoothen by calendaring if necessary.

In case of embossed PVD pigments it is preferred that the release layer is embossed with a diffractive structure.

The sheet substrate is not particularly restricted, but can be a polyester film such as polytetrafluoroethylene, polyethylene, polypropylene, and polyethylene terephthalate, a polyamide film such as 66-nylon and 6-nylon, or a peeling film such as a polycarbonate film, triacetate film, or polyamide film, or the like.

Preferably, the sheet substrate is made of polyethylene terephthalate or a copolymer thereof.

The thickness of the sheet substrate is not particularly restricted, but is preferably between 10 and 150 µm. If the thickness is 10 µm or greater, handling problems during processing will not occur, and if the thickness is 150 µm or less, the flexibility will be excellent, and problems will not occur when rolled or peeled or the like.

In a second step, a thin aluminum layer is deposited under ultra-high vacuum (UHV) conditions onto the release layer forming an aluminum foil.

This step can be repeated by deposing a further release layer on the thin aluminum foil layer and then forming another aluminum foil layer under UHV conditions on the second peeling layer.

In a third step, the coated sheet substrate is lead outside the UHV chamber into a stripping chamber under normal pressure conditions. This chamber is filled with an appropriate organic solvent and the metal foil is dissolved und therefore separated from the sheet substrate in the solvent. A further step of comminution of the metal pieces in the slurry follows until the desired size of the pigments is reached. This can be done by the impact of ultrasound of by mechanical comminution.

Steps for separating the metal pigments from release layer possibly still present in the slurry may follow, for example, by settling of the metal pieces, preferably by centrifugation followed by decantation of supernatant solvent. These steps can be repeated several times until essentially no release layer is present in the slurry. As a next step, the concentration of the solvent is adjusted to the desired value forming a PVD aluminum dispersion.

Another step may follow in which the solvent is exchanged to a solvent better suitable for the coating with the leafing additive. This can be done by solvent exchange for example.

The general production of PVD aluminum pigments is described for example in US 20030008068 A1, U.S. Pat. Nos. 6,317,947 B1, 4,321,087 A, 4,168,986 A or 3,949,139 A.

Preferred solvents used for the production of this dispersion are solvents with low boiling points (or high vacuum pressure) such as ethyl acetate, butyl acetate, acetone, isopropanol or mixtures thereof. These solvents can be more easily removed later on.

In a further step, the leafing additive can be added to the PVD pigment dispersion with organic solvent under homogenization. Thereby at least part of it is adsorbed on the surface of the PVD aluminum pigment. This step can be done at room temperature or at elevated temperatures. The leafing additive is preferably dissolved in an appropriate solvent. This solvent is preferably the same solvent as the solvent of the PVD pigment dispersion. The mixture is stirred for a certain period needed for completion of the adsorption process (reaction time). During this period, the temperature is preferably increased in a range of 30° C., preferably 40° C. up to the boiling point of the solvent. The reaction time can be in a range of 15 min to 12 hours, preferably in a range of 1 to 8 hours.

An excess of leafing additive is usually used to ensure a high extent of adsorption on the PVD pigment as the adsorption process usually underlies an adsorption/desorption equilibrium. The amount of excess leafing-additive in the solvent can be minimized by further washing steps comprising an optional addition of excess organic solvent to the leafing-PVD paste, homogenizing and then removing solvent from the dispersion. This last step can be done by first sedimenting the PVD pigments and then decanting the excess solvent in the pigment free phase. With this decantation step some-excess of the leafing additive not-bound to the PVD pigment surface is removed. This washing step can be done once or several times. However, these additional manufacturing steps are cost intensive. It is advantageous to leave a certain amount of excess leafing-additive in the effect pigment dispersion to ensure a good leafing effect by forcing the adsorption/desorption equilibrium towards adsorption of the additive on the effect pigment's surface and therefore a uniformly coated pigment surface.

Finally the concentration of the PVD aluminum pigment in this organic solvent-based dispersion may be adjusted by adding a solvent.

At the end the dispersion should have a concentration of the PVD aluminum pigment in a range of 5 to 25 wt.-% and the solvent should have a concentration of 75 to 95 wt.-%, preferably of 77 to 92 wt.-%, each based on the total PVD aluminum pigment dispersion. The concentration of excess leafing additive should not exceed about 25 wt.-% with respect to the PVD aluminum pigment as otherwise a too high concentration may have adverse effects in the final cosmetic application.

Cosmetic Oils:

The oil chosen for the PVD-aluminum pigment dispersion must be usable for skin care applications or color cosmetic applications.

Skin care applications in the course of this invention are preferably lotions, moisturizers, primers, self-tanners, face masks and face treatments, men's skin care, body paints, creams such as anti-age creams, treatment creams, balm and blemish creams (BB cream), color or complexion correction creams (CC cream) or diminish and disguise creams (DD cream).

Color cosmetic applications in the course of this invention can be summarized in two different general categories: lip color applications and eye color applications. Lip color applications are preferably lip gloss, lipstick, liquid lipstick, clear lipstick, lip cream, lip tint, lip lacquer, lip color, lip balm, lip glaze, lip paint, lip oil, lip stain, lip liner, lip polish and lip plumper.

Eye Color applications are preferably cream eye shadow, mousse eye shadow, eye shadow gel, eye shadow pencil, liquid eye shadow, liquid eyeliner, eyeliner stick, eyeliner cream, eyeliner gel, mascara, brow gel, brow pencil, brow definer and tattoo liner.

Preferred are non-aqueous based skin care or color cosmetic applications.

In this invention nail polishes are not regarded as color cosmetic applications.

The cosmetic oil usable in this invention is preferably chosen from the following types of cosmetic oils:
a) Triglycerides consisting of fatty acid esters hydrocarbon-based oils such triglycerides consisting of fatty acid esters of glycerol, in particular the fatty acids of which may have an average carbon chain length ranging from $C_8$ to $C_{36}$, and especially from $C_{12}$ to $C_{26}$, most preferred an average carbon chain length ranging from $C_{14}$-$C_{24}$, these chains possibly being linear or branched and saturated or unsaturated. With average carbon chain length, it is meant the average length of all three fatty ester carbon chains. This includes that one or two of these carbon chains may have less than, e.g. eight carbon atoms. These oils can contain mixtures of different triglyceride fatty acid esters. These oils can be synthetic or can be natural oils from plants or vegetables.
b) Mineral Oils with very high purity, wherein the hydrocarbon chains have an average length of at least 14 C-atoms.

Only very highly purified mineral oils can be used for cosmetic applications. Especially the amount of aromatic compounds in the oil needs to be less than 0.5 wt.-%, based on the total weight of mineral oil. Preferably the amount of aromatic compounds is less than 0.4 wt.-%, more preferably less than 0.3 wt.-%, even more preferably less than 0.2 wt.-% and most preferably less than 0.1 wt.-%, each based on the amount of the mineral oil.

As mineral oils usually comprise a mixture of different hydrocarbon compounds, the average chain length of the hydrocarbon chains means the average of all chain lengths in the oil.

The average length of the hydrocarbon chains is at least 14 C-atoms, more preferably 14 to 32 C-atoms and even more preferably 16 to 24 C-atoms. Below 14 C-atoms the mineral seems to be still too polar.

c) Alcohols based on alcohols other than glycerol or hydrocarbon-based (fatty) esters originating from carboxylic and alcoholic components other than glycerol according to formula (V):

$$(R^4(COO)_y)_x R^5_{y'} \quad (V)$$

Herein x is an integer and x=1 to 6, representing the number of esterified groups of the original alcoholic components with one of more than one OH-groups.

$R^4(COO)_y$ represents a carboxylic acid residue comprising 2 to 40 carbon atoms, wherein $R^4$ can be a linear or branched, saturated or unsaturated hydrocarbon chain or phenyl. It also can contain esterified or free OH-groups. The integer y can be 1 to 3. It represents the number of COOH groups of the original acidic component. For x>1 the $R^4$ chains can be the same or different chains and preferably they are the same chains.

$R^5$ represents a hydrocarbon-based chain originating from the alcoholic component or components containing from 1 to 40 carbon atoms, which can comprise a —$CH_2$—O—$CH_2$— ether unit or which can be or comprise a PPG or PEG element represented by the formula (VI)

$$(CH_2CHR^6-O)_n \quad (VI)$$

Herein $R^6$ is H or $CH_3$ and n=1 to 10, preferably 3 or 4.

Mixtures of different esters and/or alcohols can be also used.

$R^4$ has preferably 3 to 24 carbon atoms. $R^4$ can have additionally one or more amide groups and such as sarcosinates. $R^4$ and $R^5$ can independently have one or more additional hydroxyl groups that are not esterified. $R^2$ is preferably a hydrocarbon-based chain with 2 to 20 carbon atoms.

d) Fatty alcohols containing from 12 to 26 carbon atoms, for instance octyldodecanol, 2-butyloctanol, 2-hexyldecanol, 2-undecylpentadecanol, isohexacosanol and oleyl alcohol.
e) Synthetic ethers containing from 10 to 40 carbon atoms.
f) Dialkyl carbonates, the two alkyl chains possibly being identical or different.

The cosmetic oil is preferably liquid at room temperature. It is preferred that the oils have a melting point higher than 20° C. and more preferred higher than 0° C. as the dispersion of the PVD-aluminum pigments may be transported in winter at low temperatures.

The following table 1 lists examples for usable oils for this invention. Here common names and INCI names are listed as well as examples of commercially available products, where appropriate. Additionally the sum formula is given for oils of category c) and the x and y integers for esters of this category.

TABLE 1

List of examples for cosmetic oils useable in this invention according to the classification mentioned above.

| Common name | INCI-name (9th Edition CTFA Ingredient Dictionary) | Examples for commercial product names | Type of compounds | Sum formula (if possible) | x; y (only for type c) according to formula (V) |
|---|---|---|---|---|---|
| Coconut Oil, Fractionated | Caprylic/Capric Triglyceride | DUB MCT 5545; Kahloil 3005; Myritol 318 | a) | | |
| Caprylic/ Capric Triglyceride | | | | | |
| Castor oil | *Ricinus Communis* Seed Oil | Ewanol Castor Oil RI-G | a) | | |
| Sweet Almond Oil | *Prunus Amygdalus Dulcis* Oil | Ewanol SM | a) | | |
| Coriander (Seed) Oil | *Coriandrum Sativum* (Coriander) Seed Oil | | a) | | |
| Corn Oil | *Zea Mays* (Corn) Oil | | a) | | |
| Wheatgerm oil | *Triticum Vulgare* (Wheat) Germ Oil | | a) | | |
| Jojoba Oil | *Simmondsia Chinensis* (Jojoba) Seed Oil | Ewanol JO-R | a) | | |
| Grapeseed Oil | *Vitis Vinifera* (Grapd) Seed Oil | Grapeseed Oil | a) | | |
| Evening Primrose Oil | *Oenothera Biennis* (Evening Primrose) Oil | Biodemica Evening Prime Roes Oil | a) | | |
| Apricot Kernel Oil | *Prunus Armeniaca* (Apricot) Kernel Oil | Apricot Kernel Oil | a) | | |
| Avocado Oil | *Persea Gratissima* (Avocado) Oil | Avocado Oil | a) | | |
| (Hydrogenated) Palm Kernel Oil | (Hydrogenated) Palm Kernel Oil | DUB Heko Reachin CBS | a) | | |
| Babassu Oil | *Orbignya Oleifera* (Babassu) Seed Oil | Cropure Babassu oil | a) | | |
| Basil Oil | *Ocimum Basillicum* (Basil) Oil | Basil oil | a) | | |
| Hazelnut Oil | *Corylus Americana* (Hazel) Seed Oil | Hazelnut oil | a) | | |
| Hemp Oil | *Cannabis Sativa* Seed Oil | Aldiva Hemp oil Virgin | a) | | |
| Peanut Oil | *Arachis Hypogaea* (Peanut) Oil | peanut Oil | a) | | |
| Rice Bran Oil | *Oryza Sativa* (Ricd) Bran Oil | Ravi Rice Bran oil Lipovol RB | a) | | |
| Rosehip Oil | *Rosa Canina* Fruit Oil | Phytol Rtto Livopol Rtto | a) | | |
| Safflower Oil | *Carthamus Tinctorius* (Safflower) Seed Oil | CoVera SAF-Ho Rita Safflower oil | a) | | |
| Sesame Oil | *Sesamum Indicum* (Sesame) Seed Oil | Chemir Sesame oil Paryol 181 | a) | | |
| Walnut Oil | *Juglans Regia* (Walnut) Seed Oil | Phytol WAL Walnut oil | a) | | |
| Aloe Vera Oil | *Aloe Barbadensis* Leaf Extract | Aloe Vera Biovera Oil | a) | | |

TABLE 1-continued

List of examples for cosmetic oils useable in this invention according to the classification mentioned above.

| Common name | INCI-name (9th Edition CTFA Ingredient Dictionary) | Examples for commercial product names | Type of compounds | Sum formula (if possible) | x; y (only for type c) according to formula (V) |
|---|---|---|---|---|---|
| Camelina Oil Gold of pleasure oil | *Camelina Sativa* Seed Oil | Plantasens Camelina Camelina Oil | a) | | |
| Olive Oil-Certified Organic | *Olea Europaea* (Olivd) Fruit Oil | Alcogreen O Cropure Olive | a) | | |
| Organic Argan oil, sunflower oil | *Helianthus Annuus* (Sunflower) Seed Oil | Akosun Cremer oil Sunflower Oil | a) | | |
| Argan Oil | *Argania Spinosa* Kernel Oil | Ewanol AR | a) | | |
| Pumkin seed Oil | *Cucurbita Pepo* Seed Oil | Pumkin seed oil | a) | | |
| Soybean Oil | *Glycine Soja* (Soybean) Oil | Lipovol SOY | a) | | |
| Hydrogenated Rapeseed Oil | Hydrogenated Rapeseed Oil | SustOleo TSB | a) | | |
| Hydrogenated Vegetable Oil | Hydrogenated Vegetable Oil | Lipex BC | a) | | |
| Hydrogenated Soybean Oil, Hydrogenated Cottonseed Oil | Hydrogenated Soybean Oil, Hydrogenated Cottonseed Oil | Lipovol HS, Soywax Steretex NF | a) | | |
| Paraffinum Liquidium | Paraffinum Liquidium | Ewanol 204, Paraffin | b) | | |
| | Isohexadecane | | b) | $C_{16}H_{34}$ | |
| Liquid Isoparaffine | Hydrogenated Polyisobutene | | b) | | |
| Glyceryl Undecylenate | Glyceryl Undecylenate | DUB MUG | c) | $C_{14}H_{26}O_4$ | 1; 1 |
| Propanediol Dicaprylate | Propanediol Dicaprylate | DUB ZENOAT | c) | $C_{19}H_{36}O_4$ | 2; 1 |
| Propylene Glycol Dibenzoate | Propylene Glycol Dibenzoate | LexFeel Shine | c) | $C_{17}H_{16}O_4$ | 2; 1 |
| Neopentyl Glycol Diheptanoate | Neopentyl Glycol Diheptanoate | LexFeel 7 | c) | $C_{19}H_{36}O_4$ | 2; 1 |
| Isononyl nonanoate | Isononyl nonanoate | | c) | $C_{18}H_{36}O_2$ | 1; 1 |
| Isononyl Isononanoate | Isononyl Isononanoate | DUB ININ; Lanol 99; Wickenol 151 | c) | $C_{18}H_{36}O_2$ | 1; 1 |
| 2-Ethylhexyl 4-diheptanoate | 2-Ethylhexyl 4-diheptanoate | | c) | $C_{18}H_{34}O_4$ | 2; 1 |
| C12-15 Alkyl Benzoate | C12-15 Alkyl Benzoate | Jeechem-TN | c) | | |
| Isostearyl Isostearate | Isostearyl Isostearate | DUB ISIS/ Schercemol 1818 | c) | $C_{36}H_{72}O_2$ | 1; 1 |
| Hexyl laurate | Hexyl laurate | | c) | $C_{18}H_{36}O_2$ | 1; 1 |
| Isopropyl Myristate | Isopropyl Myristate | Crodamol IPM-LQ | c) | $C_{17}H_{34}O_2$ | 1; 1 |
| Myristyl myristate | Myristyl myristate | | c) | $C_{28}H_{56}O_2$ | 1; 1 |
| Diisopropyl adipate | Diisopropyl adipate | | c) | $C_{12}H_{22}O_4$ | 1; 2 |
| Decyl Isostearate (and) Isostearyl Isostearate | Decyl Isostearate (and) Isostearyl Isostearate | Crodamol SSA-LQ | c) | | |
| Oleyl Oleate | Oleyl Oleate | Schercemol OLO Ester | c) | $C_{36}H_{68}O_2$ | 1; 1 |
| Ethylhexyl Palmitate | Ethylhexyl Palmitate | Ceraphyl 368 | c) | $C_{24}H_{48}O_2$ | 1; 1 |
| Tridecyl octanoate | Tridecyl octanoate | | c) | $C_{21}H_{42}O_2$ | 1; 1 |
| Cetyl octanoate | Cetyl octanoate | | c) | $C_{24}H_{48}O_2$ | 1; 1 |

TABLE 1-continued

List of examples for cosmetic oils useable in this invention according to the classification mentioned above.

| Common name | INCI-name (9th Edition CTFA Ingredient Dictionary) | Examples for commercial product names | Type of compounds | Sum formula (if possible) | x; y (only for type c) according to formula (V) |
|---|---|---|---|---|---|
| Propylene glycol dioctanoate | Propylene glycol dioctanoate | | c) | $C_{19}H_{36}O_4$ | 2; 1 |
| Isotridecyl Isononanoate | Isotridecyl Isononanoate | | c) | $C_{22}H_{44}O_2$ | 1; 1 |
| Octyl isononanoat | Octyl isononanoat | | c) | $C_{17}H_{34}O_2$ | 1; 1 |
| Isodecyl neopentanoate | Isodecyl neopentanoate | | c) | $C_{15}H_{30}O_2$ | 1; 1 |
| Isostearyl Neopentanoate | Isostearyl Neopentanoate | Ceraphyl 375 | c) | $C_{18}H_{36}O_2$ | 1; 1 |
| 2-Octyldodecyl neopentanoate | 2-Octyldodecyl neopentanoate | | c) | $C_{25}H_{50}O_2$ | 1; 1 |
| Isopropyl stearate | Isopropyl stearate | | c) | $C_{21}H_{42}O_2$ | 1; 1 |
| Isopropyl isostearate | Isopropyl isostearate | | c) | $C_{21}H_{42}O_2$ | 1; 1 |
| Octyl stearate | Octyl stearate | | c) | $C_{26}H_{52}O_2$ | 1; 1 |
| Isooctyl stearate | Isooctyl stearate | | c) | $C_{26}H_{52}O_2$ | 1; 1 |
| 2-ethylhexyl hydroxystearate | 2-Ethylhexyl hydroxystearate | | c) | $C_{26}H_{52}O_3$ | 1; 1 |
| Isocetyl stearate | Isocetyl stearate | | c) | $C_{34}H_{68}O_2$ | 1; 1 |
| 2-octyldodecyl stearate | 2-Octyldodecyl stearate | | c) | $C_{38}H_{76}O_2$ | 1; 1 |
| Octyldodecyl Stearoyl Stearate | Octyldodecyl Stearoyl Stearate | Ceraphyl 847 | c) | $C_{56}H_{110}O_4$ | 1; 2 |
| Isopropyl Palmitate | Isopropyl Palmitate | | c) | $C_{19}H_{38}O_2$ | 1; 1 |
| 2-Ethylhexyl palmitate | 2-Ethylhexyl palmitate | | c) | $C_{24}H_{48}O_2$ | 1; 1 |
| Heptyl Undecylenate | Heptyl Undecylenate | Lexfeel Natural | c) | $C_{18}H_{34}O_2$ | 1; 1 |
| Isostearyl heptanoate | Isostearyl heptanoate | | c) | $C_{25}H_{50}O_2$ | 1; 1 |
| Pentaerythrityl Tetrabehenate | Pentaerythrityl Tetrabehenate | DUB PTB | c) | $C_{93}H_{180}O_8$ | 4; 1 |
| Isostearyl behenate | Isostearyl behenate | | c) | $C_{40}H_{80}O_2$ | 1; 1 |
| Pentaerythritol Tetraisostearate | Pentaerythritol Tetraisostearate | Crodamol PTIS/Corum 504/DUB PTIS | c) | $C_{77}H_{148}O_8$ | 4; 1 |
| | Neopentyl Glycol Diheptanoate (and) Isododecane | Lexfeel D5/ Lexfeel D4 | c) | | |
| | Pentaerythrityl Tetraethylhexanoate | DUP PTO | c) | $C_{37}H68O_8$ | 4; 1 |
| | Dipentaerythrityl Pentaisononanoate | DUB VINYL | c) | | 5; 1 |
| | Dipentaerythrityl Hexaisononanoate | | | $C_{58}H_{106}O_{13}$ | 6; 1 |
| | Tetraethylene glycol diheptanoate | | c) | $C_{22}H_{42}O_7$ | 2; 1 |
| | Neopentyl Glycol Diheptanoate | DUB DNPG | c) | $C_{19}H_{36}O_4$ | 2; 1 |
| | Propylene glycol 2-ethyl hexanoate | | c) | $C_{15}H_{28}O_4$ | 1; 1 |
| | Dicapryl Succinate | SustOleo DCS | c) | | 1; 2 |
| | Isopropyl lauroyl sarcosinate | | c) | $C_{18}H_{35}NO_3$ | 1; 1 |
| | Triisostearyl Citrate | Schercemol TISC | c) | $C_{60}H_{116}O_7$ | 1; 3 |
| | Diisostearyl Malate | Schercemol DISM Ester | c) | $C_{40}H_{78}O_5$ | 1; 2 |

TABLE 1-continued

List of examples for cosmetic oils useable in this invention according to the classification mentioned above.

| Common name | INCI-name (9th Edition CTFA Ingredient Dictionary) | Examples for commercial product names | Type of compounds | Sum formula (if possible) | x; y (only for type c) according to formula (V) |
|---|---|---|---|---|---|
| | Bis-Diglyceryl Polyacyladipate-1 | Kahloil 6448 | c) | | |
| | Diisopropyl Dimer Dilinoleate | Schercemol DID | c) | $2\times(C_{21}H_{38}O_2)$ | 1; 1 (Dimer) |
| | Diisopropyl Sebacate | Schercemol DIS Ester | c) | $C_{16}H_{30}O_4$ | 1; 2 |
| | Trimethylolpropane Tricaprylate/ Tricaprate | LexFeel 21 | c) | $C_{30}H_{56}O_6$/ $C_{36}H_{68}O_6$ | 3; 1 |
| | Diheptyl Succinate (anc) Capryloyl Glycerin/Sebacic Acid Copolymer | LexFeel N-20 | c) | | |
| Pentaerythrityl adipate/ caprate/capryl ate/heptanoate | Polyester 4 | LexFeel 700 | c) | | |
| | cocyl adipidic acid/ trimethylolpropane copolymer | Schercemol CATC | c) | | |
| Octyldodecanol | Octyldodecanol | DUB ODOL/ Tegosoft G20 | d) | $C_{20}H_{43}OH$ | |
| | Dicaprylyl Ether | Cetiol OE | e) | $C_{16}H_{34}O$ | |
| | Dicaprylyl Carbonate | Cetiol CC (Cognis) | f) | | |
| | Oleyl erucate, | | c) | $C_{40}H_{76}O_2$ | 1; 1 |
| | PPG-3 Benzyl Ether Ethylhexanoate | Crodamol SFX-LQ | c) | $C_{18}H_{28}O_3$ | 2; 1 |
| | PPG-3 Benzyl Ether Myristate | Crodamol STS-LQ | c) | $C_{24}H_{40}O_3$ | 2; 1 |

A preferred group of a cosmetic oil of type a) consists of castor oil, almond oil, wheat germ oil, jojoba oil, apricot oil, soya bean oil or canola oil, (hydrogenated) palm kernel oil, capric/caprylic triglyceride (coconut oil) and mixtures thereof.

A preferred group for an oil of type b) consists of isohexadecane or hydrogenated polyisobutene and mixtures thereof.

A preferred group for an oil of type c) consists of isodecyl neopentanoate; isononyl nonanoate; isononyl isononanoate; isopropyl stearate, isopropyl isostearate, 2-ethylhexyl hydroxystearate, 2-octyldodecyl stearate, isostearyl isostearate, isostearyl heptanoate, isopropyl myristate, isopropyl palmitate, pentaerythritol tetraisostearate oleyl oleate and mixtures thereof.

A preferred group for an oil of type d) consists of octyldodecanol, isohexacosanol or mixtures thereof.

The amount of aromatic compounds in the cosmetic oil is preferably less than 0.5 wt.-%, based on the total weight of oil. More preferably the amount of aromatic compounds is less than 0.4 wt.-%, even more preferably less than 0.3 wt.-%, further even more preferably less than 0.2 wt.-% and most preferably less than 0.1 wt.-%, each based on the amount of the cosmetic oil.

Higher amounts or aromatic compounds are likely not acceptable in the cosmetic formulations intended for the use of the PVD aluminum pigment dispersion.

In preferred embodiments of the effect pigment dispersion, the oil suitable for cosmetic skin applications has a boiling point of at least 75° C. at normal conditions (pressure 1.013 bar). Cosmetic oils with such boiling point are likely to be well separable from the organic solvent of the original PVD aluminum pigment dispersion. Preferably, the boiling point is higher than 100° C. and more preferably higher than 130° C. It is also possible that the oil has no defined boiling point as it decomposes before boiling. Such oils are of course well separable form the organic solvents used in the original PVD aluminum pigment dispersion.

Dispersion of Leafing-PVD Aluminum Pigment and Cosmetic Oil:

The amount of the PVD-aluminum pigment is in a range of 8 to 30 wt.-% and the amount of the oil is in a range of 70 to 90 wt.-%, each based on the total weight of the effect pigment dispersion and the amount of excess leafing additive is in a range of 0 to 25 wt.-%, based on the total weight of the PVD aluminum pigment.

In preferred embodiments of the effect pigment dispersion, the amount of PVD aluminum pigment is in a range of 12.5 to 25 wt-% and the amount of the oil in a range of 75 to 87.5 wt.-%, each based on the total weight of the effect pigment dispersion.

In preferred embodiments the amount of PVD-aluminum pigment is in a range of 14 to 22 wt.-% and the amount of cosmetic oil is in a range of 77 to 85 wt-% oil, each based on the total weight of the effect pigment dispersion, whilst the amount of excess leafing additive is in a range of 1 to 20 wt.-%, based on the total weight of the PVD aluminum pigment.

In further embodiments the amount of PVD-aluminum pigment is in a range of 15 to 21 wt.-% and the amount of cosmetic oil is in a range of 77 to 83 wt-% oil, each based on the total weight of the effect pigment dispersion, whilst the amount of excess leafing additive is in a range of 2 to 15 wt.-%, based on the total weight of the PVD aluminum pigment.

The PVD aluminum pigment will agglomerate to a great extent at concentrations higher than 30 wt.-%. If on the other hand the concentration is less than 8 wt.-% the hiding power, and therefore the effectiveness of the pigment, will be too low.

The excess of the leafing additive should be minimized, as too much excess may adversely influence the properties of the final cosmetic formulation. On the other hand, it is advantageous to leave a certain amount of excess leafing-additive in the effect pigment dispersion to ensure a good leafing effect by forcing the adsorption/desorption equilibrium towards adsorption of the additive on the effect pigment's surface and therefore a uniformly coated pigment surface.

In preferred embodiments the amount of excess leafing additive is in a range of 1 to 22 wt.-%, more preferred in a range of 2 to 20 wt.-%, even more preferred in a range of 4 to 18 wt.-% and most preferred in a range of 7 to 13 wt.-%, each based on the total weight of the PVD aluminum pigment.

Besides these three main components, the effect pigment dispersion also can optionally comprise further additives such as dispersing additives or antioxidant additives, residues of organic solvent, binders for cosmetic applications or fillers.

Typically an antioxidant can be added in order to avoid the formation of bacteria and/or ageing of the cosmetic oil. It would be added typically in an amount of 0 to 0.5 wt.-%, preferably 0.05 to 0.3 and more preferably of 0.02 to 0.2 wt.-%, each based on the total weight of the effect pigment dispersion.

Residual organic solvents may be present, if the removal of organic solvent from the effect pigment dispersion was not completed. The concentration of excess organic solvent is less than 5 wt.-%, preferably less than 4 wt.-%, more preferably less than 3 wt.-%, even more preferably less than 2 wt.-%, most preferably less than 1 wt.-%, and very most preferably less than 0.5 wt.-%, each based on the total weight of the effect pigment dispersion.

Additional dispersing additives may be present in the dispersion in small amounts in order to better stabilize the PVD aluminum pigments against agglomeration. With additional dispersing additives, other additives than those used for providing the leafing effect are meant, although the leafing-additives might have also dispersing properties. The concentration of additional dispersing additives in the oily dispersion is preferably in a range of 0 to less than 0.5 wt.-% and more preferably 0 to 0.2 wt.-%, based on the weight of the PVD aluminum pigment.

In concentrations above 0.5 wt.-% the leafing effect may be decreased as these additives compete with the leafing additives in the adsorption on the PVD pigment surface.

The PVD aluminum pigment dispersion may in certain embodiments additionally contain a compound usable as binder or film former in an intended final cosmetic skin care or color cosmetic application. In such cases, the binder may ensure better compatibility of the leafing PVD aluminum pigment and the components of the cosmetic formulation. Preferably, the concentration of the binder is kept as low as possible and preferably in a range of 0.0 to less than 1 wt.-%, based on the total weight of the effect pigment dispersion.

Furthermore, the PVD aluminum pigment dispersion may additionally contain fillers from the group of natural or synthetic mica, glass flakes, glass spheres, silica spheres or flakes or alumina spheres or flakes. These fillers mainly are beneficial for the skin feeling of the final cosmetic formulation and for the consistency of the formulation. Additionally the platelet-shape of these fillers may add a delicate pearlescent effect to the optical appearance of the final cosmetic formulation.

This kind of fillers may be present in an amount in a range of 5 to 60 wt.-%, preferably in a range of 10 to 56 wt.-% and more preferably in a range of 15 to 30 wt.-%, based on the weight of PVD aluminum pigment.

In a preferred embodiment, the PVD aluminum dispersion does not contain these fillers, but they may be added to the final cosmetic formulation.

In preferred embodiments the weight of the PVD-aluminum pigment, the leafing additive, the cosmetic oil suitable for cosmetic skin care or color cosmetic applications and optionally the filler all together is at least 90 wt.-%, more preferred at least 95 wt.-% even more preferred at least 96 wt.-% and most preferred at least 98 wt.-%, based on the total weight of the effect pigment dispersion.

In preferred embodiments the PVD aluminum pigment dispersion is not encapsulated by microcapsules made from polymers as described, for example in WO 2013/10776 or WO 2017/037716 A2. In such microcapsules effect pigments may be encapsulated by certain polymers such as polyacrylates or cellulose derivates. First of all the concentration of pigment in such known microcapsules is much too high for PVD pigments. The technology of forming the polymer shells around the effect pigment is not suitable for a leafing metal pigment. Also, the polymer shell may interact with the PVD aluminum pigment in that it disturbs the leafing effect.

Further preferred embodiments are directed to an effect pigment dispersion comprising a PVD-aluminum pigment, a leafing additive and an oil suitable for cosmetic skin care or color cosmetic applications, wherein
  a) the amount of the PVD-aluminum pigment is in a range of 8 to 30 wt.-%, b) the amount of the oil is in a range of 70 to 90 wt.-%, each based on the total weight of the effect pigment dispersion and
  c) the leafing additive is partly adsorbed on the surface of the PVD-aluminum pigment and partly an excess additive dissolved in the oil, wherein the amount of excess leafing additive is in a range of 0 to 25 wt.-%, based on the weight of PVD aluminum pigment
  wherein the amount of excess organic solvent is less than 1 wt.-%, based on the total weight of the effect pigment dispersion and the amount of aromatic compounds is less than 0.1 wt.-%, based on the amount of cosmetic oil.

In a further preferred embodiment of the PVD aluminum dispersion the leafing additive chosen is an additive according to formula (II) with a monocetylphosphoric acid ester or dicetylphosphoric acid ester ($R=C_{16}$) or mixtures thereof.

The effect pigment dispersion is produced by a method comprising the following subsequent steps:
  a) providing a leafing PVD-aluminum dispersion in an organic solvent,
  b) adding the oil suitable for cosmetic skin care or color cosmetic applications to the dispersion a) and
  c) removing the organic solvent, optionally under vacuum.

Step a) of this method has already been described in detail in the section dealing with the leafing PVD aluminum pigment.

Step b) of this method is uncritical and should be done under stirring.

Step c) is preferably done under increased temperature. Preferred temperatures are in a range of 45 to 80° C., depending on the organic solvent. It can be done optionally under vacuum. The removal of the organic solvent can be preferably done in a solvent exchanger.

Further optional components of the PVD effect pigment dispersion as described above are preferably added after the removal of the organic solvent as otherwise they may be affected by the removal step.

A further embodiment of this invention is an effect pigment dispersion as described above for use as an effect pigment semi-finished product in a cosmetic skin care or a color cosmetic formulation.

A further embodiment of this invention is the use of the effect pigment dispersion as described above as a semi-finished product in cosmetic skin or color cosmetic formulations.

The term "semi-finished product" here simply reflects that PVD-aluminum pigments need to be offered as a dispersion because of their high agglomeration tendency.

The cosmetic skin or color cosmetic formulations are those mentioned above.

Preferred cosmetic skin or color cosmetic formulations are selected from the following groups:
a) skin care selected from the group consisting of lotions, primer, face masks and face treatments, body paints, men's skin care, balm and blemish cream (BB cream), color or complexion correction cream (CC cream) and diminish and disguise cream (DD cream);
b) lip color formulations selected from the group consisting of lip gloss, liquid lipstick, clear lipstick, lip cream, lip tint, lip lacquer, lip color, lip balm, lip glaze, lip paint, lip oil, lip stain, lip liner, lip polish and lip plumper and
c) eye color formulations selected from the group consisting of cream eye shadow, mousse eye shadow, eye shadow gel, liquid eye shadow, liquid eyeliner, eyeliner cream, eyeliner gel, mascara, brow gel or lash primer.

Even more preferred cosmetic skin or color cosmetic formulations are selected from the following groups:
a) skin care selected from the group consisting of face masks and face treatments, body paints, men's skin care and color or complexion correction cream (CC cream);
b) lip color formulations selected from the group consisting of lip gloss, liquid lipstick, clear lipstick, lip cream, lip tint, lip lacquer, lip glaze, lip paint, lip oil, lip liner, lip polish and lip plumper and
c) eye color formulations selected from the group consisting of cream eye shadow, mousse eye shadow, eye shadow gel, liquid eye shadow, liquid eyeliner, eyeliner cream, eyeliner gel, mascara, brow gel or lash primer.

Cosmetic Skin Care or Color Cosmetic Formulation:

The PVD leafing-aluminum dispersion can be part of a cosmetic skin care or color cosmetic formulation. The cosmetic formulations and their preferred embodiments are the same as mentioned in the previous sections.

In this kind of cosmetic formulations the leafing-effect of the aluminum pigments can lead to a strong mirror effect in the case of flat PVD pigments or to a strong rainbow effect in the case of embossed PVD aluminum pigments. The formulations have a consistency, which is "liquid" enough to allow the PVD-pigments to orient themselves well when applied to the human skin. These formulations do not tolerate organic solvents for the reasons mentioned previously.

These cosmetic formulations will contain ingredients or adjuvants, which are typical for the respective formulations and well known to the skilled artisan. Typically, these ingredients can comprise any of emollients, waxes, skin conditioning agents, vitamins, trace elements, moisturizers, stiffening agents, sequestering agents, fragrances, fillers, preservatives, antioxidants, surfactants, binders, film formers, thickeners or gelling agents.

Some ingredients may have several of those functions in the formulation. The oils used in the effect pigment dispersion may also have one of more of the functions mentioned above, e.g. they may act as an emollient. In this case, the amounts of other components acting as emollient should be adjusted. Also, it should be realized that a platelet-like effect pigment like a leafing-PVD aluminum pigment would influence, for example, the viscosity of the cosmetic formulation. This fact should be taken into account, as it may result in different concentrations of some of the ingredients compared to formulations without effect pigments. Additionally or alternatively, some additives may be added which have a viscosity reducing-properties and which are cosmetically acceptable.

It is preferred that in cosmetic formulations according to this invention the addition of thickeners is minimized or avoided. Otherwise, the viscosity of the formulation may be too high, which would disturb the orientation of the PVD aluminum pigments, leading to a dramatic loss of either the mirror or the rainbow effect.

Such thickeners are typically platelet-like or rod-like clays, such as layered silicates or layered aluminosilicates. Examples of such thickeners are smectites, such as montmorillonites, bentonites, sepiolites, saponites, hectorites, beidellites, or layered silicates from the class of the vermiculites. These layered silicates have hydrated exchangeable cations with high exchange capacities and are commonly used as thickeners in many cosmetic formulations.

Not contained in this kind of substances are the group of fillers consisting of natural or synthetic mica, glass flakes, glass spheres, silica spheres or flakes or alumina spheres or flakes.

Additionally, all components based on silicones should be either avoided or minimized in the cosmetic formulation. Such silicon-oils are not suitable as the oil of the effect pigment dispersion. Thus, their general use in the cosmetic formulation is possible in some cases, but they should be handled with care.

In such cases, silicon oils with high densities, low viscosities and a low polarity are preferred. Generally such silicon oils should be used in concentrations as low as possible in the cosmetic formulation.

The concentration of the PVD-aluminum pigment in the skin care or color cosmetic formulation is typically in a range of 0.8 to 5 wt.-%, preferably in a range of 1.0 to 4 wt.-% and most preferably in a range of 1.2 to 3.5 wt.-%, each based on the total cosmetic composition.

A further embodiment of the present invention is a method of producing a cosmetic skin or color cosmetic formulation comprising the steps:
a) preparing a phase A by mixing typical ingredients characteristic for the formulation,
b) providing a phase B comprising or consisting of the effect pigment dispersion of this invention, c) mixing and homogenizing phase A and phase B, optionally at temperatures above 20° C., under low mechanical stress conditions and finally d) pouring or filling the formulation into an appropriate container or packaging.

In step a) all the ingredient characteristic for the respective cosmetic skin care or color cosmetic formulation are mixed in their appropriate amounts. Usually they are just added subsequently and homogenized.

This step may also be divided by first preparing two or more phases of different ingredients. These two or more phases may be added together to form phase A.

Alternatively one of more of these phases or components may also be added to the cosmetic formulation after step b) or step c), although this is usually not necessary.

In most cases step b) simply involves to provide an effect pigment dispersion in a cosmetic oil as described above. If additional components such e.g. as fillers or antioxidants are needed, they may be added already at the point of production of the PVD-aluminum dispersion, before or in step b), or just shortly before step c) of this method.

Additionally, further components, like e.g. another oil, which are part of the desired cosmetic formulation can be added to the PVD aluminum pigment dispersion at this step.

Step c) must be done under low mechanical stress conditions in order not to damage or destroy the shear sensitive PVD aluminum pigments.

This means, for example, mixing using a butterfly mixer or a planetary mixer.

EXAMPLES

A Preparation of Leafing PVD-Aluminum Pigments:

Example 1a

In a thermostatic controlled 1 L reactor 300 g of Metalure A 41010 AE (commercially available dispersion of flat PVD-aluminum pigment in acetic acid ethyl ester (solid content 10 wt.-% with a $D_{50}$ (Horiba LA-930)=9.5 µm to 10.5 µm, from ECKART GmbH)) were dispersed in 240 g acetic acid ethyl ester at a stirring rate of 200 rpm/min and were heated to 40° C. Subsequently 5.4 g phosphoric acid cetylester (CAS number: 3539-43-3, Hostaphat CC 100, Clariant) dissolved in 30 g acetic acid ethyl ester were added to the aluminum pigment dispersion. After 6 h of stirring under boiling solvent, the mixture was cooled down to room temperature. Finally, acetic acid ethyl ester was added to yield a final dispersion of 6 wt.-% of the PVD-aluminum pigment.

Example 2a

In a thermostatic controlled 1 L reactor 198 g of Silverdream Prismatic H-50550 (commercially available dispersion of embossed PVD-aluminum pigment in acetic acid ethyl ester, solid content 5 wt.-% with a $D_{50}$ (Horiba LA-930)=about 50 µm, from ECKART America) were dispersed in 249 g acetic acid ethyl ester at a stirring rate of 200 rpm/min and were heated to 60° C. Subsequently 3 g phosphoric acid cetylester (CAS number: 3539-43-3, Hostaphat CC 100, Clariant) dissolved in 20 g acetic acid ethyl ester were added to the aluminum pigment dispersion. After 6 h of stirring at 60° C. the mixture was cooled down to room temperature. Finally, acetic acid ethyl ester was added to yield a final dispersion of 5 wt.-% of embossed PVD-aluminum pigment.

B Preparation of PVD-Aluminum Pigment Dispersions in Cosmetic Oil

Examples 3-15 and Comparative Examples 16 to 24

80 g of an oil according to table 2 were added to 322 g of the dispersion of Example 1a and homogenized. Subsequently the solvent was evaporated under vacuum (about 100 mbar). The temperature was raised continuously during this process until a final temperature of about 50 to 60° C. was reached. The residual amount of solvent was in a range of 2 to 4 wt.-%. Finally a dispersion with about 20 wt.-% of aluminum pigment in the respective oil was obtained. The mirror effect of these dispersions was evaluated by the method described in the next section and the results are depicted in tables 2 and 3.

Examples 25 to 37 and Comparative Examples 38 to 46

80 g of an oil according to table 2 were added to 400 g of the dispersion of Example 2a and homogenized. Subsequently the solvent was evaporated under vacuum (100 mbar). The temperature was raised continuously during this process until a final temperature of about 50 to 60° C. was reached. The residual amount of solvent was in a range of 2 to 4 wt.-%. Finally a dispersion with about 19.5 wt.-% of aluminum pigment in the respective oil was obtained. The diffractive effect of these dispersions was evaluated by the method described in the next section and the results are depicted in table 2.

The oils used were the same for Example 3 and 17, for Example 4 and 18 and so on.

C Test methods of Mirror Effect:

C.1 Mirror Like Effect of Oil Dispersion

The optical properties of the dispersion of all examples based on the flat PVD-aluminum pigments of Example 1a were evaluated by visual appearance in a beaker using the following grading scale:

1: dull and grey appearance
2: dull and slightly silver appearance
3: silver appearance with certain brilliancy
4: good brilliancy
5: mirror like effect with high brilliancy.

All Examples noted as 5 or 4 are scored to fulfill the desired properties of optical appearance of the pigments of this invention. As viscosities are very different between the different oils, with a direct impact on a common drawdown application, the evaluation by visual appearance of the pure dispersion was used.

A very good mirror effect was attributed to the undisturbed formation of the leafing effect of the PVD-aluminum pigment in the cosmetic formulation.

For all Examples based on the diffractive PVD-aluminum effect pigment of Example 2a, the visual appearance of the diffractive effect of the oily dispersion was evaluated in a beaker. Here the scale starts from 1: no diffractive effect
2: slight diffractive effect
3: good diffractive effect
4: high diffractive effect with brilliancy
5: extremely high diffractive effect with brilliancy.

All Examples noted here as 5, 4 or 3 are scored to fulfill the desired properties of optical appearance of the pigment of this invention.

C.2 Mirror Like Effect in Final Formulation/Application

The optical properties of the final formulation were evaluated by visual appearance. In case of a flat PVD-aluminum pigment the scale started from 1 (dull and grey appearance) to 5 (mirror like effect with high brilliancy). All examples noted as 5 or 4 were better than present state-of-the-art. In case of a diffractive PVD-aluminum pigment the scale started from 1 (dull appearance, no diffractive effect) to 5 (extremely high diffractive effect). All examples noted as 5 to 3 were better than present state-of-the-art. As the mirror effect can be affected by the surface of the packaging, the cosmetic application was applied to the skin, spread using a spatula and then evaluated according to the upper mentioned scale. A very good mirror effect was attributed to the formation of the leafing effect of the PVD-aluminum pigment in the cosmetic formulation applied on the skin.

The results of the cosmetic formulations are shown in table 13.

TABLE 2

Mirror effect and diffractive effect for Examples of PVD-aluminum effect pigment dispersions in cosmetic oils.

| Examples | Oil | Mirror Effect in dispersion for flat pvd-pigment | Diffractive Effect in dispersion for diffractive pvd-pigment |
|---|---|---|---|
| 3 and 25 | Isononyl Isononanoate | 5 | 5 |
| 4 and 26 | Alkyl benzoate | 5 | 4 |
| 5 and 27 | Paraffinum Liquidum (Ewanol 204) | 5 | 4 |
| 6 and 28 | Paraffinum subliquidum (Jäkelchemie)) | 4 | 3 |
| 7 and 29 | Isohexadecane | 5 | 4 |
| 8 and 30 | Isopropyl myristate | 5 | 4 |
| 9 and 31 | Isopropyl palmitate | 5 | 4 |
| 10 and 32 | Hydrogenated Polyisobutene | 5 | 4 |
| 11 and 33 | Capric/Caprylic Triglyceride | 4 | 3 |
| 12 and 34 | Pentaerythritol Tetraisostearate | 4 | 3 |
| 13 and 35 | Octyldodecanol | 4 | 3 |
| 14 and 36 | Isostearyl isostearate | 4 | 3 |
| 15 and 37 | Castor oil | 4 | 3 |

COMPARATIVE EXAMPLES

TABLE 3

Mirror effect and diffractive effect for Comparative Examples of PVD-aluminum effect pigment dispersions in cosmetic oils.

| Comparative Example | Oil | Mirror Effect in dispersion | Diffractive Effect in dispersion for diffractive pvd-pigment |
|---|---|---|---|
| Comparative 16 and 38 | Glycerine > 85% | 5, but pigment did not disperse homogeneously and built a mirror on the top due to incompatibility with glycerine. | 5, but pigment did not disperse homogeneously and built a mirror on the top due to incompatibility with glycerine |
| 17 and 39 | Isopropanol * | 3 | 2 |
| 18 and 40 | Isododecane | 2 | 1 |
| 19 and 41 | Caprylyl Methicone | 1 | 1 |
| 20 and 42 | C12-C15 Alkyl Benzoate, Stearalkonium Bentonite, Propylene Carbonate | 3 | 2 |
| 21 and 43 | Hydrogenated Polyisobutene, Ethylene/Propylene/Styrene Copolymer, Butylene/Ethylene/Styrene Copolymer | 3 | 2 |
| 22 and 44 | Isohexadecane with 5-20% Garamite | 1 | 1 |
| 23 and 45 | Cyclopentasiloxane | 1 | 1 |
| 24 and 46 | Dimethicone | 1 | 1 |

* Here a dispersion of PVD pigment in isopropanol (METALURE A 41010 IL, Eckart America) was used originally to produce the leafing PVD pigment according to Example 1a. No additional oil was added.

The cosmetic oils used in the Examples of table 2 generally yielded very good (5) or good (4) results with respect to the gloss observed in the beaker the dispersion was filled in. The gloss can be attributed to a pronounced leafing-effect. Generally, the Examples with a diffractive PVD-pigment seemed to be a little bit weaker in the appearance compared to the Examples using flat PVD-pigments.

Comparative Examples 16 and 38 using glycerine as cosmetic oil were not satisfying in the sense that the leafing PVD-aluminum pigments did not mix with glycerine and built a mirror on the top of the liquid. Such phase separated mixtures cannot be used in practice as semi-finished effect pigment dispersion for cosmetic uses.

Isopropanol, used in Comparative Examples 17 and 39, is merely a solvent and not a cosmetic oil and also did not lead to a good gloss effect. All Comparative Examples using siloxane-based cosmetic oils (Comp. Examples 19, 41, 23, 45 24 and 46) yielded bad results. Here, the leafing-effect is assumed to be destroyed because of the very low surface tension of these unpolar oils.

In Comparative Examples 22 and 44 the cosmetic oil additionally contained a filler based on a delaminated silicate platelets. These kind of fillers do have an adverse effect on the gloss, as here the leafing properties of the PVD aluminum pigment are again destroyed. In Comparative Examples 18 and 44 isododecane was used as oil. It is assumed that this cosmetic oil is too unpolar D Preparation of Different Skin Care or Color Cosmetic Applications:

The following Examples for cosmetic skin care or color cosmetic applications were formulated. Usually the PVD-pigment dispersion of Example 3 was used in the inventive Examples.

Example 47: Gloss Cream Eye Shadow

TABLE 4

Components and their ratios of the formulation

| Phase | INCI Name | Component | Product Name | wt % |
|---|---|---|---|---|
| A | Octyldodecanol | Emollient | Tegosoft G20 | 10 |
|  | Isostearyl Isostearate | Emollient | Schercemol 1818 | 6 |
|  | Bis-Diglyceryl Polyacyladipate-2 | Skin Conditioning Agent, Emollient | Softisan 649 | 10 |
|  | Octyldodecyl Stearoyl Stearate | Emollient | Ceraphyl 847 | 5 |
|  | Bees Wax | Wax, Stiffening Agent | Ewacera 12 | 10 |
|  | Isopropyl Lanolate | Skin Conditioning Agent, Emollient | Ewalan IO | 8 |
|  | Tocopheryl Acetate | Antioxidant | dl-alpha-Tocopheryl Acetate | 1 |
| B | Synthetic Fluorphlogopite | Filler | Synafil S 1050 (Eckart GmbH) | 5 |
|  | Aluminum Powder (and) Isononyl Isononanoate | Effect Pigment Dispersion | Leafing aluminum pigment dispersion according to Example 3 | 45 |
|  |  |  | Sum: | 100 |

Phase A was made by adding the appropriate amounts of the components mentioned above and heated under stirring to 85° C. Phase B was made by adding and homogenizing the appropriate amount of a synthetic mica as a filler (Synafil S 1050 from Eckart GmbH) to the dispersion obtained from Example 3. Subsequently Phase B was added slowly to phase A at 85° C. and both phases were homogenized and then poured into an appropriate container and cooled down to room temperature.

Example 48: Body Oil

TABLE 5

Components and their ratios of the formulation

| Phase | INCI Name | Component | Product Name | wt.-% |
|---|---|---|---|---|
| A | Caprylic/Capric Triglyceride | Emollient | Tegosoft CT | 25.0 |
|  | Ethylhexyl Stearate | Emollient | Cetiol 868 | 22.5 |
|  | Isopropyl Palmitate | Emollient | Isopropylpalmitate | 20.0 |
|  | Dicaprylyl Carbonate | Emollient | Cetiol CC | 7.0 |
|  | Tocopherol | Antioxidant | Copherol F 1300 C | 0.5 |
| B | Aluminum Powder (and) Isononyl Isononanoate | Effect Pigment Dispersion | Leafing aluminum pigment dispersion according to Example 3 | 25.0 |
|  |  |  | Sum: | 100.0 |

Phase A was made similar to Example 47. No synthetic fluorphlogopite was added in phase B as a filler. After homogenization of phase A, phase B was added slowly and homogenized. Finally, the mixture was poured into an appropriate container and cooled down to room temperature.

Example 49: Lip Cream with Low Viscosity

TABLE 6

Components and their ratios of the formulation

| Phase | INCI Name | Component | Product Name | wt.-% |
|---|---|---|---|---|
| A | Isohexadecane | Emollient | Isohexadecane | 51 |
| B | Pentaerythritol Tetraisostearate | Emollient | Crodamol PTIS-LQ-(MV) | 8 |
|  | Beeswax | Wax, Stiffening Agent | Kahlwax 8138 | 3 |
|  | Isononyl isononanoate | Emollient | Wickenol 151 | 6 |
|  | Glyceryl Dibehenate (and) Tribehenin (and) Glyceryl Behenate | Wax, Stiffening Agent | Compritol 888 CG Pellets | 6 |
|  | Caprylyl Glycol | Preservative | Lexgard O | 1 |
| C | Aluminum Powder (and) Isononyl Isononanoate | Effect Pigment Disperison | Leafing aluminum pigment dispersion according to Example 3 | 25 |
|  |  |  | Sum: | 100 |

Phase A was heated under stirring to 80° C. and subsequently Phase B was added slowly. After homogenization phase C was added and again homogenized.

Example 50: Lip Gloss

TABLE 7

Components and their ratios of the formulation

| Phase | INCI Name | Component | Product Name | wt.-% |
|---|---|---|---|---|
| A | Hydrogenated Polyisobutene (and) Ethylene/Propylene/Styrene Copolymer (and) Butylene/Ethylene/Styrene Copolymer | Gelled Emollients | Versagel ME 1600 | 55 |
|  | Caprylic/Capric Triglyceride | Emollient | Labrafac CC | 8 |
|  | Phenylpropyldimethyl-siloxysilicate | Film Former | Silshine 151 | 7 |
|  | Caprylyl Methicone | Conditioning Agent | Silsoft 034 | 5 |
| B | Almuminum powder (and) Isononyl Isononanoate | Effect Pigment Dispersion | Leafing aluminum pigment dispersion according to Example 3 | 25 |
|  |  |  | Sum: | 100 |

This formulation was made in the same way as Example 47, except that no synthetic fluorophlogopite was added in phase B as a filler.

Comparative Example 51a and b: Gloss Cream Eye Shadow (to Example 47)

TABLE 8

Components and their ratios of the formulation

| Phase | INCI Name | Component | Product Name | wt.-% |
|---|---|---|---|---|
| A | Octyldodecanol | Emollient | Tegosoft G20 | 10 |
|  | Isostearyl Isostearate | Emollient | Schercemol 1818 | 6 |
|  | Bis-Diglyceryl Polyacyladipate-2 | Skin Conditioning Agent, Emollient | Softisan 649 | 10 |
|  | Octyldodecyl Stearoyl Stearate | Emollient | Ceraphyl 847 | 5 |
|  | Bees Wax | Wax, Stiffening Agent | Ewacera 12 | 10 |
|  | Isopropyl Lanolate | Emollient | Ewalan IO | 8 |
|  | Tocopheryl Acetate | Antioxidant | dl-alpha-Tocopheryl Acetate | 1 |
| B | Synthetic Fluorphlogopite | Filler | Synafil S 1050 (Eckart GmbH) | 5 |
|  | Aluminum Powder (and) Silica | Effect Pigment | Visionaire Splendid Silver Sea (Eckart GmbH) | 45 |
|  |  |  | Sum: | 100 |

This formulation was made in the same way as Example 47, but a conventional commercially available aluminum pigment (Visionaire Splendid Silver Sea) for cosmetic industry was used instead of the PVD pigment of Example 1 a. In Comp. Example 43a the pigment was used as produced (non-leafing) and in Comp. Example 43b a leafing treatment similar as in Example 1a was made.

Comparative Example 52: Lip Cream with Garamite (to Example 49)

TABLE 9

Components and their ratios of the formulation

| Phase | INCI Name | Component | Product Name | wt.-% |
|---|---|---|---|---|
| A | Isohexadecane | Emollient | Isohexadecane | 41 |
| B | Quaternium-90 Sepiolite (and) Quaternium-90 Montmorillonite | Thickener, Stabilisation Agent | Garamite-7308 XR | 7 |
|  | Pentaerythritol Tetraisostearate | Emollient | Crodamol PTIS-LQ-(MV) | 8 |
|  | Beeswax | Wax, Stiffening Agent | Kahlwax 8138 | 3 |
|  | Isononyl isononanoate | Emollient | Wickenol 151 | 6 |
|  | Glyceryl Dibehenate (and) Tribehenin (and) Glyceryl Behenate | Wax, Stiffening Agent | Compritol 888 CG Pellets | 5 |
|  | Caprylyl Glycol | Preservative | Lexgard O | 1 |
|  | Hydrogenated Polyisobutene (and) Ethylene/Propylene/Styrene Copolymer (and) Butylene/Ethylene/Styrene Copolymer | Gelled Emollients | Versagel ME 750 | 4 |
| C | Aluminum Powder (and) Isonony Isononanoate | Effect Pigment Dispersion | Leafing aluminum pigment dispersion according to Example 3 | 25 |
|  |  |  | Sum: | 100 |

This formulation was made in the same way as Example 49, except that additionally Garamite-7308 XR was added to phase B as thickener.

Comparative Example 53: Gel-to-Powder

TABLE 10

Components and their ratios of the formulation

| Phase | INCI Name | Component | Product Name | wt.-% |
|---|---|---|---|---|
| A | Cyclopentasiloxane | Emollient | Xiameter PMX-0245 | 46.4 |
|  | Quaternium-90 Sepiolite (and) Quterunium-90 Montmorrillonite | Thickener, Stabilisation Agent | GARAMITE-7308 XR | 0.8 |
|  | Polysilicone-11 (and) Laureth-12 | Mattifier, Sensory Agent | Gransil EP-LS | 4.0 |
| B | Cyclopentasiloxane (and) Stearoxymethicone/Dimethicone Copolymer (and) Dimethicone | Mattifier, Sensory Agent | GI CD-10 | 14.0 |
|  | Isododecane (and) Polysilicone-11 | Mattifier, Sensory Agent | Gransil PC-12 | 14.0 |
| C | Aluminum Powder (and) Isonony Isononanoate | Effect Pigment Dispersion | Leafing aluminum pigment dispersion according to Example 3 | 20.0 |

TABLE 10-continued

Components and their ratios of the formulation

| Phase | INCI Name | Component | Product Name | wt.-% |
|---|---|---|---|---|
| D | Phenoxyethanol, Ethylhexylglycerin | Preservative | Euxyl PE 9010 | 0.8 |
|   |   |   | Sum: | 100.0 |

Phase A and phase B were homogenized in separate containers. Subsequently phase B was added to phase A under stirring and the pH was adjusted to 6.5 with a citric acid solution (10 wt.-%). Subsequently phases C and D were added slowly and the formulation was homogenized and filled into a suitable container.

This formulation proved to be not suitable, as the leafing effect did not develop in powder form.

Comparative Example 54: Gloss Cream Eye Shadow with Solvent Based PVD Dispersion (to Example 47)

TABLE 11

Components and their ratios of the formulation

| Phase | INCI Name | Component | Product Name | wt % |
|---|---|---|---|---|
| A | Octyldodecanol | Emollient | Tegosoft G20 | 5 |
|   | Isostearyl Isostearate | Emollient | Schercemol 1818 | 3 |
|   | Bis-Diglyceryl Polyacyladipate-2 | Skin Conditioning Agent, Emollient | Softisan 649 | 5 |
|   | Octyldodecyl Stearoyl Stearate | Emollient | Ceraphyl 847 | 2 |
|   | Bees Wax | Wax, Stiffening Agent | Ewacera 12 | 5 |
|   | Isopropyl Lanolate | Emollient | Ewalan IO | 4 |
|   | Tocopheryl Acetate | Antioxidant | dl-alpha-Tocopheryl Acetate | 0.5 |
| B | Synthetic Fluorphlogopite | Filler | Synafil S 1050 (Eckart GmbH) | 2 |
|   | Aluminum Powder (and) Ethyl Acetate (and) Cetyl phosphate | Effect Pigment Dispersion | Leafing aluminum pigment dispersion according to Example 1a | 72.5 |
|   |   |   | Sum: | 100 |

This formulation was made in the same way as Example 47, except that instead of Example 3, the commercially available PVD-aluminum dispersion (Metalure A-41010 AE, Eckart America) in ethyl acetate treated with Hostaphat CC was used (see Example 1a).

The formulation was extremely soft and it etched and softened the packaging, which was made from a plastic typically used for such kind of formulations, in an undesirable manner. The solvent brought into the formulation with the PVD dispersion smelled strongly.

Thus, this formulation was not suitable as a gloss cream eye shadow.

Comparative Example 55: Lip Gloss with Solvent Based PVD Dispersion (to Example 50)

TABLE 12

Components and their ratios of the formulation

| Phase | INCI Name | Component | Product Name | wt % |
|---|---|---|---|---|
| A | Hydrogenated Polyisobutene (and) Ethylene/Propylene/Styrene Copolymer (and) Butylene/Ethylene/Styrene Copolymer | Gelled Emollients | Versagel ME 1600 | 35 |
|   | Caprylic/Capric Triglyceride | Emollients | Labrafac CC | 5 |
|   | Phenylpropyldimethylsiloxysilicate | Film Former | Silshine 151 | 4 |
|   | Caprylyl Methicone | Skin Conditioning Agent | Silsoft 034 | 3 |
| B | Almuminum powder (and) (and) Ethyl Acetate (and) Cetyl phosphate | Effect Pigment Disperison | Leafing aluminum pigment dispersion according to Example 1a | 53 |
|   |   |   | Sum: | 100 |

This formulation was made in the same way as Example 50, except that instead of Example 3, a commercially available PVD-aluminum dispersion (Eckart America) in ethyl acetate treated with Hostaphat CC according to the procedure of Example 1a was used.

An extremely strong mirror effect developed after application to the lips. However, the formulation has an extremely liquid consistency and after pouring the formulation into the container this plastic material was immediately attacked by the formulation. Furthermore, the lip gloss exhibited an undesired strong smell due to the organic solvent.

TABLE 13

Results of Mirror effect on skin applications

|   | Kind of cosmetic formulation | Mirror effect on skin |
|---|---|---|
| Example |   |   |
| 47 | Gloss cream Eye shadow | Very Good 5 |
| 48 | Body Oil | Very good 5 |
| 49 | Lip cream without Garamite low viscosity | Very good 5 |
| 50 | Lip Gloss | Very good 5 |
| Comparative Examples |   |   |
| 51a | Gloss cream Eye shadow | Very bad 1 |
| 51b | Gloss cream Eye shadow | Very bad 1 |
| 52 | Lip cream with garamite | Very bad 1 |
| 53 | Gel-to-powder | Bad 2 |
| 54 | Cream eye shadow with solvent based | Satisfying 3 |

TABLE 13-continued

Results of Mirror effect on skin applications

| | Kind of cosmetic formulation | Mirror effect on skin |
|---|---|---|
| 55 | PVD dispersion Lip gloss with solvent based PVD dispersion | Very good 1 |

All the Examples 47 to 50 exhibited a very good mirror effect with high gloss and a high brilliance, which indicates a well-developed leafing effect of the PVD aluminum pigments.

Comparative Examples 51a and b are, like Example 47, a gloss cream eye shadow, but Visionaire Splendid Silver Sea (Eckart GmbH) used here is a conventional aluminum pigment which has not been produced by a PVD process. Therefore, the mirror effect is essentially not present compared to Example 47. Interestingly no significant difference in the optical properties was observed between using the non-leafing pigment (51a) or the pigment after leafing treatment (51 b).

In Comparative Example 52 the lip cream formulation contained Garamite-7308 XR, a thickener based on delaminated silicates. The mirror effect turned out to be very poor, especially when compared to Example 49. Such kind of thickeners have a strong impact on the viscosity of the formulation. They can easily increase the viscosity to such extent, that a good orientation of the effect pigment is no longer possible.

Comparative Example 53 was a gel-to-powder formulation. Here a good gloss and therefore a good leafing effect was observed in the formulation, but not in the application on the skin. The reason is probably, that during the application the gel transforms to a powder which did not have enough liquid components to develop the leafing effect of the PVD aluminum pigment.

Comparative Example 54 had at least a satisfying leafing effect in the skin application, but the disadvantages mentioned above like bad smell and attacking the container material due to the organic solvent make this Comparative Example not suitable for a commercial product.

The same argumentation applies for Comparative Example 55, although here the mirror effect in the lip application was very good.

The invention claimed is:

1. An effect pigment dispersion comprising a PVD-aluminum pigment, a leafing additive and an oil suitable for cosmetic skin care or color cosmetic applications, wherein
    a) the amount of the PVD-aluminum pigment is in a range of 8 to 30 wt.-%,
    b) the amount of the oil is in a range of 70 to 90 wt.-%, each based on the total weight of the effect pigment dispersion and
    c) the leafing additive is partly adsorbed on the surface of the PVD-aluminum pigment and partly present in an excess amount dissolved in the oil, wherein the excess amount is in a range of 0 to 25 wt.-%, based on the weight of PVD aluminum pigment.

2. The effect pigment dispersion according to claim 1, further comprising a residual organic solvent present in an amount of less than 5 wt.-% of the total weight of the effect pigment dispersion.

3. The effect pigment dispersion according to claim 1, further comprising a filler including any one or more of natural mica, synthetic mica, glass flakes, glass spheres, silica spheres, silica flakes, alumina spheres, alumina flakes, and talc.

4. The effect pigment dispersion according to claim 1, wherein the sum of the weights of the PVD-aluminum pigment, the leafing additive, and the oil is at least 90 wt.-%, based on the total weight of the effect pigment dispersion.

5. The effect pigment dispersion according to claim 1, wherein the amount of PVD aluminum pigment is in a range of 12.5 to 25 wt-% and the amount of the oil in a range of 75 to 87.5 wt.-%, each based on the total weight of the effect pigment dispersion.

6. The effect pigment dispersion according to claim 1, wherein the leafing additive includes any one or more of:
    a) a phosphoric ester of the formula (I):

$$(R-O)_m-P(O)(OR^1)_{(3-m)} \qquad (I),$$

b) a phosphonic acid ester of the general formula (II):

$$R-P(O)(OR^2)(OR^3) \qquad (II)$$

wherein m is 1 to 3 or any mixture thereof,
    R independently represent a linear or branched alkyl with a carbon chain in a range of $C_8$ to $C_{20}$,
    $R^1$ independently represent H or a linear or branched alkyl with a carbon chain in a range of $C_1$ to $C_6$, wherein when m is 1, $R^1$ are identical or different, and
    $R^2$ and $R^3$ independently represent H or a linear or branched alkyl with a carbon chain in a range of $C_1$ to $C_6$, wherein $R^2$ and $R^3$ are identical or different,
    c) a fatty acid with the general formula (III)

$$R'-COOH \qquad (III)$$

wherein R' is a linear or branched alkyl with a carbon chain in a range of $C_{12}$ to $C_{26}$, or a mixture thereof, and
    d) an organofunctional silane according to formula (IV):

$$R''-Si(OR^7)_3 \qquad (IV)$$

wherein $R^7$ is a linear of branched alkyl moiety with a carbon chain in a range of $C_1$ to $C_4$, and R" is a linear or branched alkyl or aryl moiety with a carbon chain in a range of $C_8$ to $C_{24}$.

7. The effect pigment dispersion according to claim 6, wherein the leafing additive includes any one or more of:
    a) the phosphoric ester of the formula (I), wherein m is 1, 2, or a mixture thereof, $R^1$ is H, and R independently represent a linear or branched alkyl with a carbon chain in a range of $C_{12}$ to $C_{18}$, and
    b) the phosphonic acid ester of the formula (II), wherein $R^2$ and $R^3$ are H and R independently represent a linear or branched alkyl with a carbon chain in a range of $C_{10}$ to $C_{18}$.

8. The effect pigment dispersion according to claim 2, wherein aromatic compounds from said residual solvent are present in the amount of less than 0.5 wt. %, based on the total weight of oil.

9. The effect pigment dispersion according to claim 1, wherein the oil includes any one or more of:
    a) triglyceride including fatty acid ester chains having average chain lengths ranging from $C_8$ to $C_{36}$, the fatty acid ester chains being any one or more of linear, branched, saturated, and unsaturated;
    b) a very high purity mineral oil, wherein the mineral oil includes hydrocarbon chains having an average length of at least 14 C-atoms;

c) an alcohol other than glycerine or a hydrocarbon-based fatty ester originating from carboxylic acid and alcoholic components other than glycerol according to formula (V):

$$(R^4(COO)_y)_x R^5_{y'} \quad (V)$$

wherein x is an integer from 1 to 6 representing the number of acidic groups for an alcoholic component with more than one OH-group, $R^4(COO)$ represents a carboxylic acid residue comprising from 2 to 40 carbon atoms, wherein $R^4$ independently represent a linear or branched, saturated or unsaturated hydrocarbon chain or a phenyl group, y is an integer from 1 to 3 representing the number of COOH groups of an original acidic component;

$R^5$ independently represent a hydrocarbon-based chain originating from the alcoholic component, containing from 1 to 40 carbon atoms, and comprising any one or more of a —$CH_2$—O—$CH_2$— ether unit, a PPG element, and a PEG element, the PPG element and PEG element being represented by the formula (VI):

$$(CH_2CHR^6-O)_n \quad (VI)$$

wherein $R^6$ independently represent H or $CH_3$ and n is 1 to 10;

d) a fatty alcohol containing from 12 to 26 carbon atoms;
e) a synthetic ether containing from 10 to 40 carbon atoms, and
f) a dialkyl carbonate identical or different alkyl chains.

10. The effect pigment dispersion according to claim 1, wherein the PVD-aluminum pigment is a leafing pigment with planar surfaces.

11. The effect pigment dispersion according to claim 1, wherein the PVD-aluminum pigment comprises an embossed structure with a period in a range from 5,000 to 20,000 lines per cm.

12. The effect pigment dispersion according to claim 1, further comprising a filler, wherein the sum of the weights of the PVD-aluminum pigment, the leafing additive, the oil, and the filler is at least 90 wt.-%, based on the total weight of the effect pigment dispersion.

13. The effect pigment dispersion according to claim 6, wherein $R^1$ independently represent a linear or branched alkyl with a carbon chain in a range of $C_1$ to $C_3$.

14. The effect pigment dispersion according to claim 6, wherein $R^2$ and $R^3$ independently a linear or branched alkyl with a carbon chain in a range of $C_1$ to $C_3$.

15. The effect pigment dispersion according to claim 6, wherein R' is a linear or branched alkyl with a carbon chain in a range of $C_{14}$ to $C_{24}$, or a mixture thereof.

16. The effect pigment dispersion according to claim 6, wherein $R^7$ is a linear of branched alkyl moiety with a carbon chain in a range of $C_1$ to $C_3$.

17. The effect pigment dispersion according to claim 6, wherein $R^7$ is a linear of branched alkyl moiety with a carbon chain in a range of $C_1$ to $C_2$.

18. The effect pigment dispersion according to claim 6, wherein R" is a linear or branched alkyl or aryl moiety with a carbon chain in a range of $C_{12}$ to $C_{18}$.

19. The effect pigment dispersion according to claim 7, wherein the leafing additive includes the phosphonic acid ester of the formula (II), wherein R is a linear or branched alkyl with a carbon chain in a range of $C_{12}$ to $C_{16}$.

20. A cosmetic skin care formulation comprising the effect pigment dispersion according to claim 1 and one or more of a binder and a film former.

21. A lip color formulation comprising a lip color cosmetic formulation including the effect pigment dispersion according to claim 1.

22. An eye color formulation comprising an eye color cosmetic formulation including the effect pigment dispersion according to claim 1.

23. A method of producing an effect pigment dispersion, the method comprising:
providing a leafing PVD-aluminum dispersion in an organic solvent, the dispersion comprising a PVD-aluminum pigment and a leafing additive,
adding an oil suitable for cosmetic skin or color cosmetic applications to the PVD-aluminum dispersion, and
removing the organic solvent,
wherein the amount of the PVD-aluminum pigment is in a range of 8 to 30 wt.-%, the amount of the oil is in a range of 70 to 90 wt.-%, each based on the total weight of the dispersion, and
the leafing additive is partly adsorbed on the surface of the PVD-aluminum pigment and partly present in an excess amount dissolved in the oil, wherein the excess amount is in a range of 0 to 25 wt.-%, based on the weight of PVD aluminum pigment.

24. The method according to claim 23, wherein removing the organic solvent comprises removing the organic solvent under vacuum.

25. A method of producing a cosmetic skin or color cosmetic formulation, the method comprising:
preparing a phase A by mixing formulation ingredients,
providing a phase B comprising an effect pigment dispersion, the effect pigment dispersion comprising a PVD-aluminum pigment, a leafing additive and an oil suitable for cosmetic skin care or color cosmetic applications, wherein the amount of the PVD-aluminum pigment is in a range of 8 to 30 wt.-%, the amount of the oil is in a range of 70 to 90 wt.-%, each based on the total weight of the effect pigment dispersion, and
the leafing additive is partly adsorbed on the surface of the PVD-aluminum pigment and partly present in an excess amount dissolved in the oil, wherein the excess amount is in a range of 0 to 25 wt.-%, based on the weight of PVD aluminum pigment,
mixing and homogenizing phase A and phase B to prepare a cosmetic formulation, and
pouring or filling the cosmetic formulation into a container or packaging.

26. The method according to claim 7, wherein mixing and homogenizing phase A and phase B is performed at temperatures above 20° C. under low mechanical stress conditions.

* * * * *